United States Patent [19]
Padilla et al.

[11] Patent Number: 6,152,918
[45] Date of Patent: Nov. 28, 2000

[54] LASER DEVICE WITH AUTO-PIERCING TIP FOR MYOCARDIAL REVASCULARIZATION PROCEDURES

[75] Inventors: Henry N. Padilla, Hollister; Richard L. Mueller, Byron; Stuart D. Harman, San Jose, all of Calif.

[73] Assignee: Eclipse Surgical Technologies, Inc., Sunnyvale, Calif.

[21] Appl. No.: 09/058,387

[22] Filed: Apr. 9, 1998

Related U.S. Application Data

[63] Continuation-in-part of application No. 08/628,849, Apr. 5, 1996, Pat. No. 5,738,680, and a continuation-in-part of application No. 08/675,698, Jul. 3, 1996, Pat. No. 5,766,164, and a continuation-in-part of application No. 08/664,956, Jun. 13, 1996, and a continuation-in-part of application No. 08/794,733, Feb. 3, 1997, Pat. No. 6,027,497, and a continuation-in-part of application No. 09/031,752, Feb. 27, 1998, abandoned.

[60] Provisional application No. 60/051,272, Jun. 30, 1997.

[51] Int. Cl.$^7$ ...................................................... A61B 18/18
[52] U.S. Cl. .................................. 606/15; 606/7; 606/41; 606/167; 606/185
[58] Field of Search ............................... 606/2, 7, 10, 11, 606/13–16, 167, 181, 182, 184, 185, 186, 41, 45, 48, 49, 50

[56] References Cited

U.S. PATENT DOCUMENTS

| | | |
|---|---|---|
| 4,072,147 | 2/1978 | Hett . |
| 4,657,018 | 4/1987 | Hakky . |
| 4,658,817 | 4/1987 | Hardy . |
| 4,669,467 | 6/1987 | Willett et al. . |
| 4,706,656 | 11/1987 | Kuboto . |

(List continued on next page.)

FOREIGN PATENT DOCUMENTS

| | | |
|---|---|---|
| 0 515 867 | 12/1992 | European Pat. Off. . |
| 807417 | 5/1997 | European Pat. Off. . |
| 0 812574 A2 | 12/1997 | European Pat. Off. . |
| WO 92/10142 | 6/1992 | WIPO . |
| WO 93/20742 | 10/1993 | WIPO . |
| WO 95/17127 | 6/1995 | WIPO . |
| WO 96/35469 | 11/1996 | WIPO . |
| WO 99/04708 | 2/1999 | WIPO . |
| WO 99/20187 | 4/1999 | WIPO . |
| WO 99/22655 | 5/1999 | WIPO . |

*Primary Examiner*—Linda C. M. Dvorak
*Assistant Examiner*—Bryan K. Yarnell
*Attorney, Agent, or Firm*—Ilene Lapidus Janofsky; Ross M. Carothers

[57] ABSTRACT

The apparatus for combined mechanical/laser myocardial revascularization of a human heart includes: inserting a mechanical piercing device and an elongated flexible lasing apparatus into the chest cavity of a patient; mechanically auto-piercing, micro-tearing or spreading the epicardium of the heart; and then lasing from beneath the epicardium through the myocardium. The apparatus is guided to an area exterior to a ventricle of the patient's heart, and the distal end of the energy delivery device such as an optical fiber apparatus is placed internal to the exterior wall of the heart through an opening which has been created by mechanically piercing, micro-tearing or spreading the epicardium, so that the myocardium and not the epicardium is irradiated with laser energy to allow passage of said energy delivery device such as an optical fiber distal end or said laser energy into the left ventricular cavity without causing a laser irradiation of the epicardium which might be a cause of operative bleeding and for better allowing the sealing of the epicardium after the apparatus is removed. The apparatus includes a hand-held device controllable by the physician having a removable distal head portion with an auto-piercing mechanism and can use a vacuum source to provide a suction force at the head portion. The auto-piercing mechanism is implemented by various ways such as a spring-biased actuating member in the TMR hand-held device and an electromechanical operated piercing mechanism. The hand-held TMR device with handle assembly can also be controlled by a computer to provide auto- sequencing of the auto-piercing needle mechanism and the laser firing with auto-fiber advancement.

28 Claims, 16 Drawing Sheets

U.S. PATENT DOCUMENTS

| | | |
|---|---|---|
| 4,718,417 | 1/1988 | Kittrell et al. . |
| 4,846,171 | 7/1989 | Kauphausman et al. . |
| 4,913,142 | 4/1990 | Kittrell et al. ............................. 606/7 |
| 4,967,745 | 11/1990 | Hayes et al. . |
| 5,041,108 | 8/1991 | Fox et al. ................................. 606/15 |
| 5,217,454 | 6/1993 | Khoury ..................................... 606/14 |
| 5,380,316 | 1/1995 | Aita ........................................... 606/7 |
| 5,389,096 | 2/1995 | Aita ........................................... 606/15 |
| 5,425,355 | 6/1995 | Kulick ....................................... 606/14 |
| 5,431,628 | 7/1995 | Millar ........................................ 604/100 |
| 5,549,601 | 8/1996 | McIntyre et al. ......................... 606/15 |
| 5,562,603 | 10/1996 | Moll et al. ................................ 600/204 |
| 5,573,531 | 11/1996 | Gregory .................................... 606/14 |
| 5,607,421 | 3/1997 | Jeevanandam et al. . |
| 5,703,985 | 12/1997 | Owyang ................................... 385/117 |
| 5,713,894 | 2/1998 | Murphy-Chutorian et al. .......... 606/15 |
| 5,725,521 | 3/1998 | Mueller ..................................... 606/7 |
| 5,738,680 | 4/1998 | Mueller et al. ........................... 606/15 |
| 5,766,164 | 6/1998 | Mueller et al. ........................... 606/15 |
| 5,782,823 | 7/1998 | Mueller ..................................... 606/7 |
| 5,785,702 | 7/1998 | Murphy-Chutorian et al. .......... 606/7 |
| 5,807,383 | 9/1998 | Kolesa et al. ............................. 606/7 |
| 5,832,929 | 11/1998 | Rudko et al. .............................. 606/7 |
| 5,899,915 | 5/1999 | Saadat ....................................... 606/170 |
| 5,913,853 | 6/1999 | Loeb et al. ................................ 606/15 |
| 5,997,531 | 12/1999 | Loeb et al. ................................ 606/13 |
| 6,019,756 | 2/2000 | Mueller et al. ............................ 606/7 |

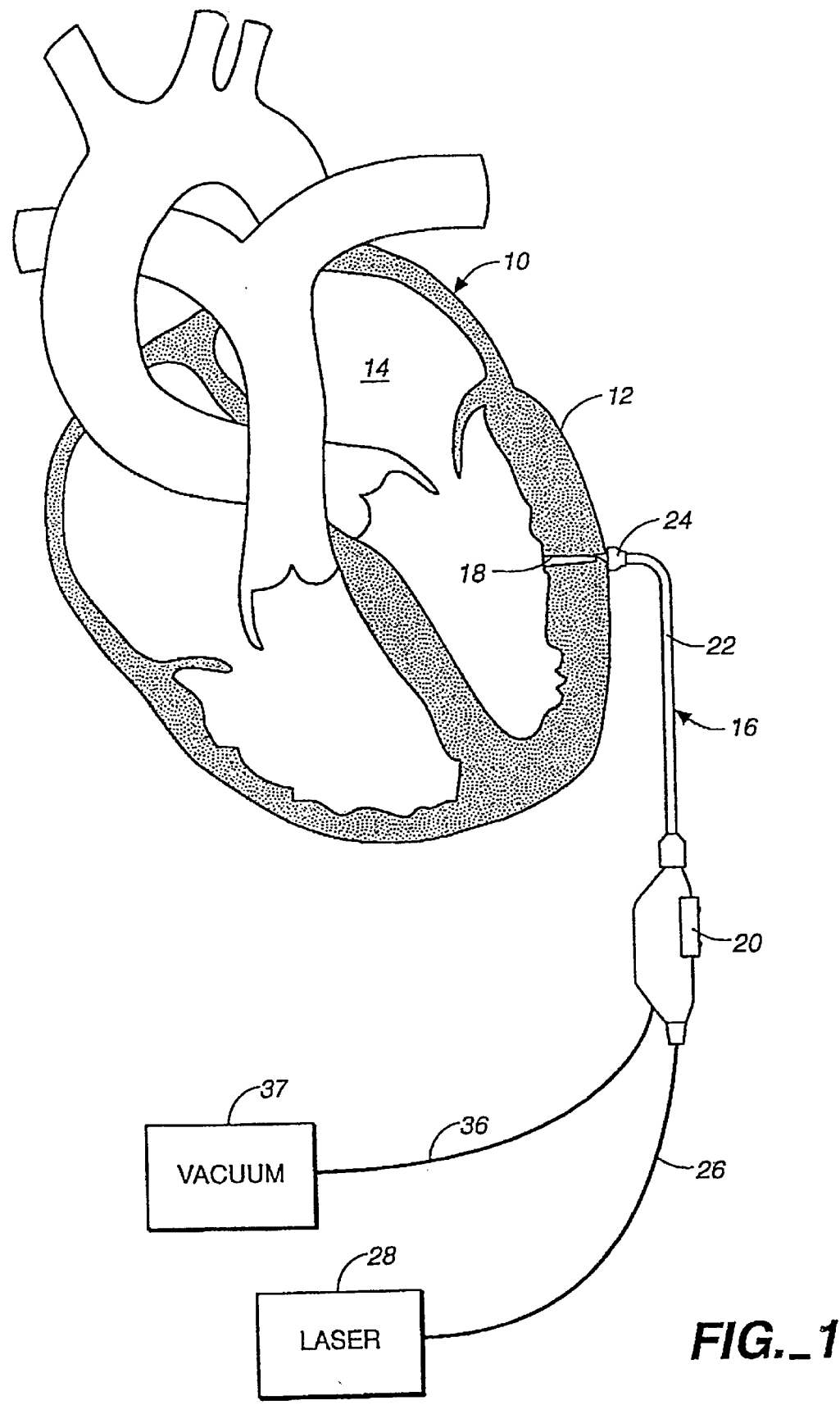
FIG._1

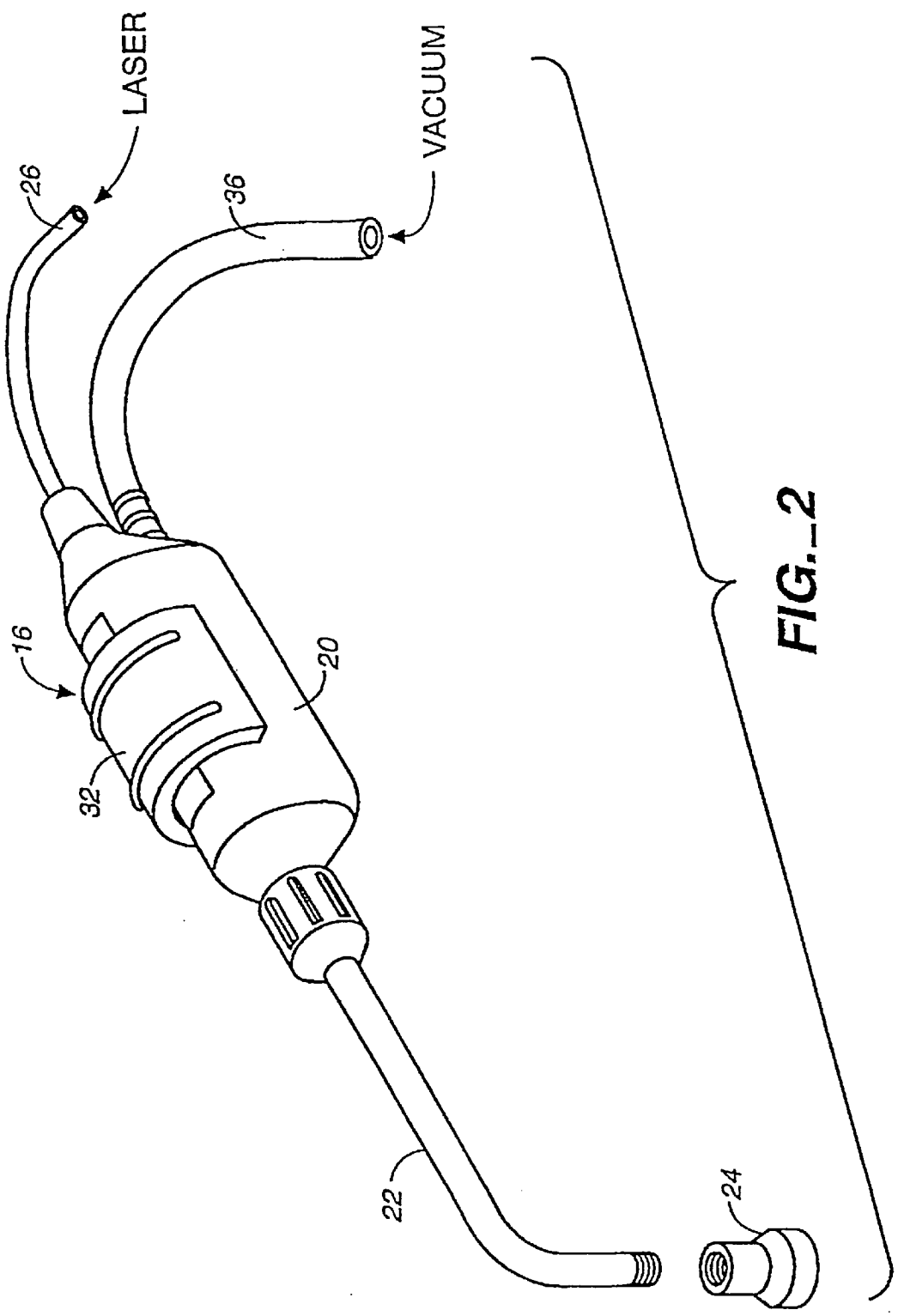
FIG._2

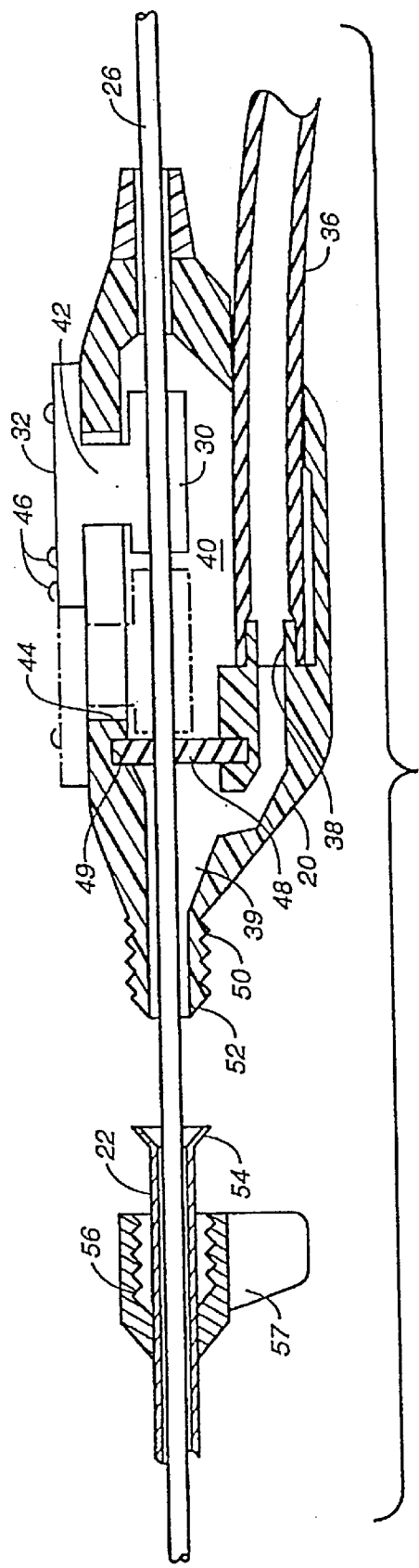
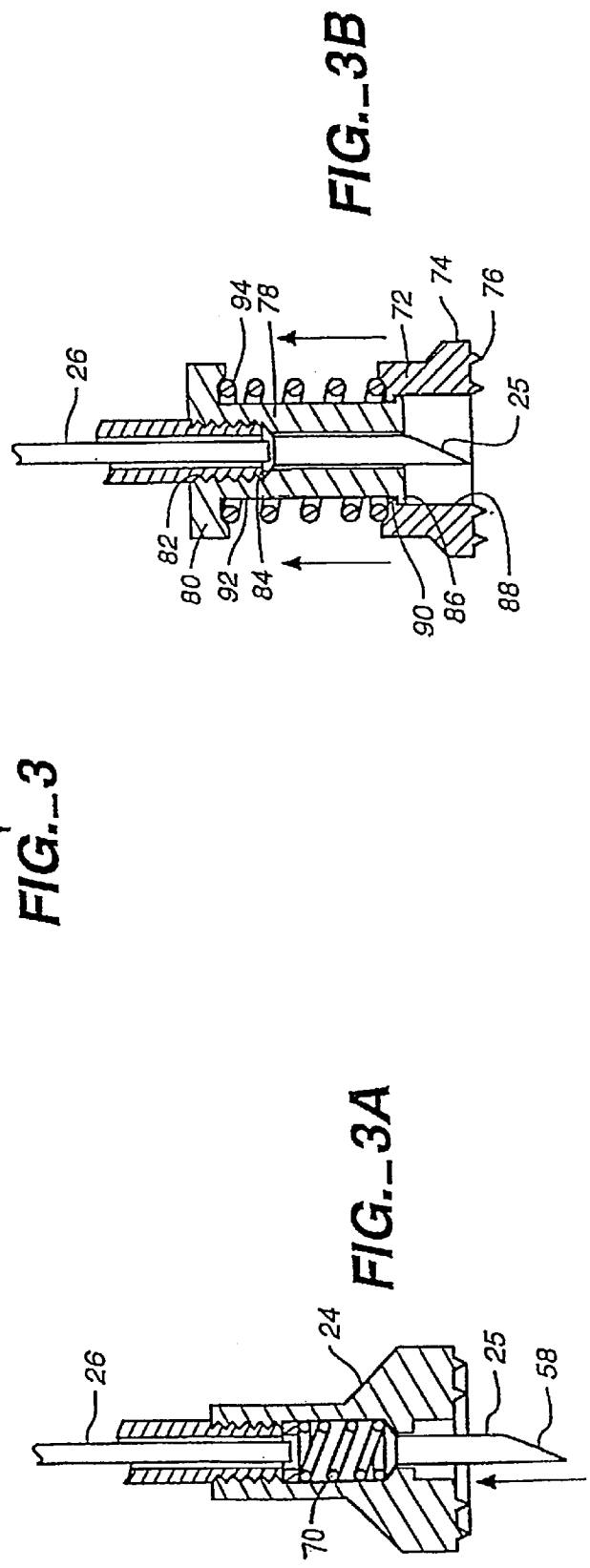

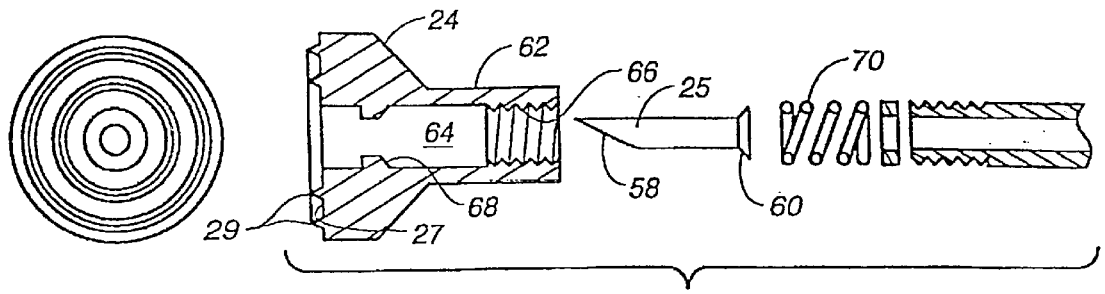
FIG._4  FIG._5
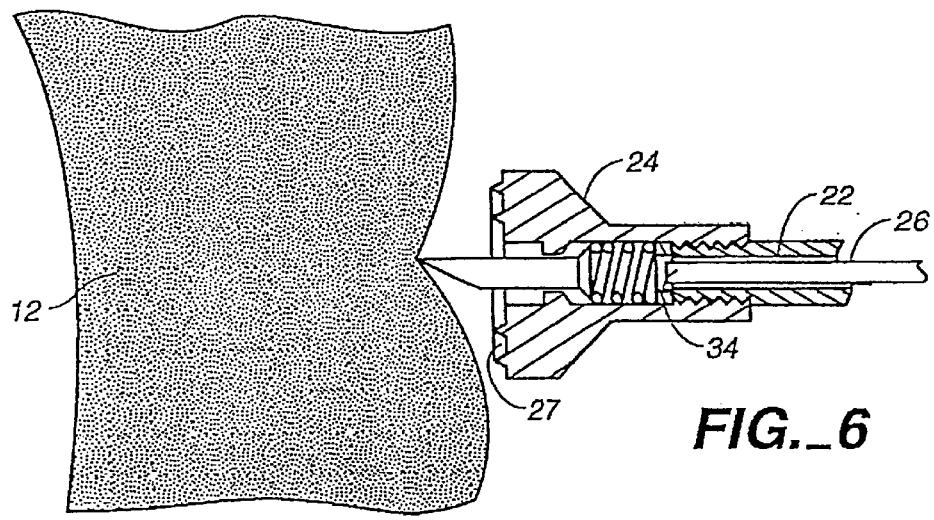
FIG._6
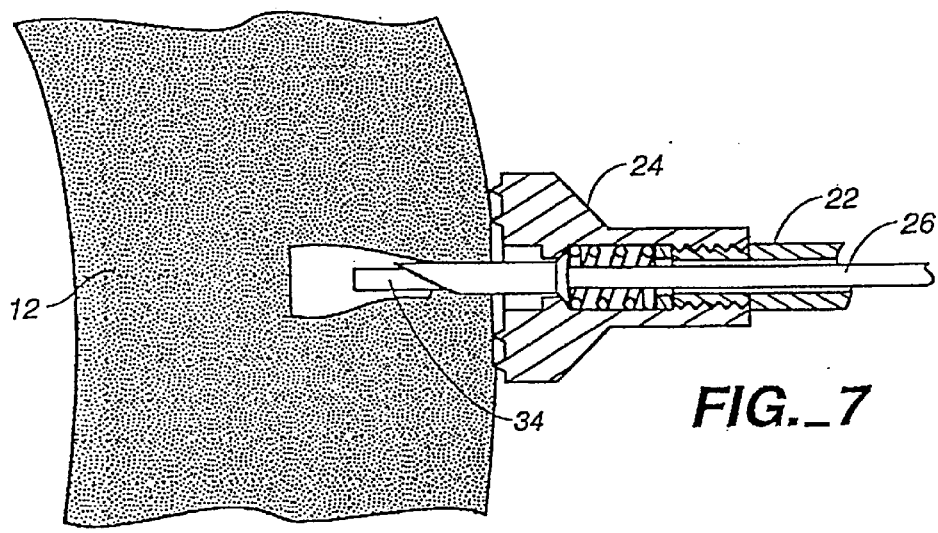
FIG._7

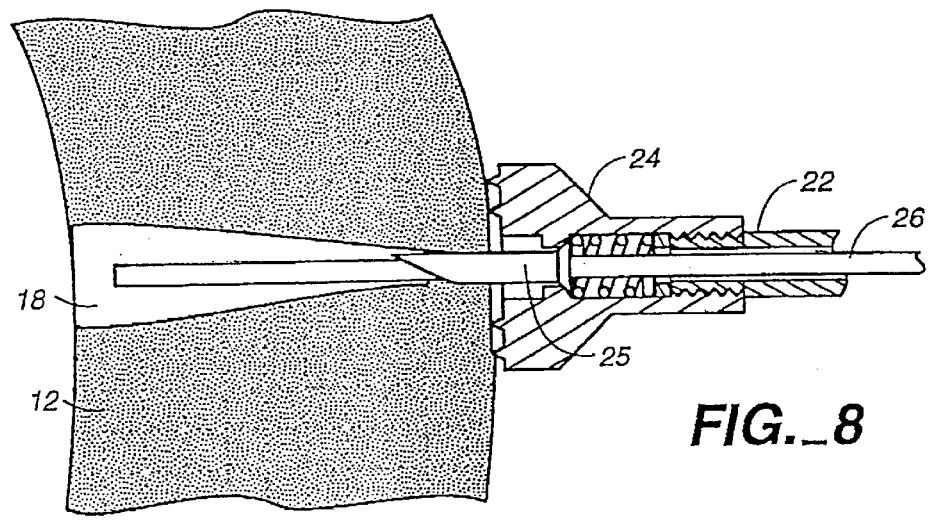
FIG._8
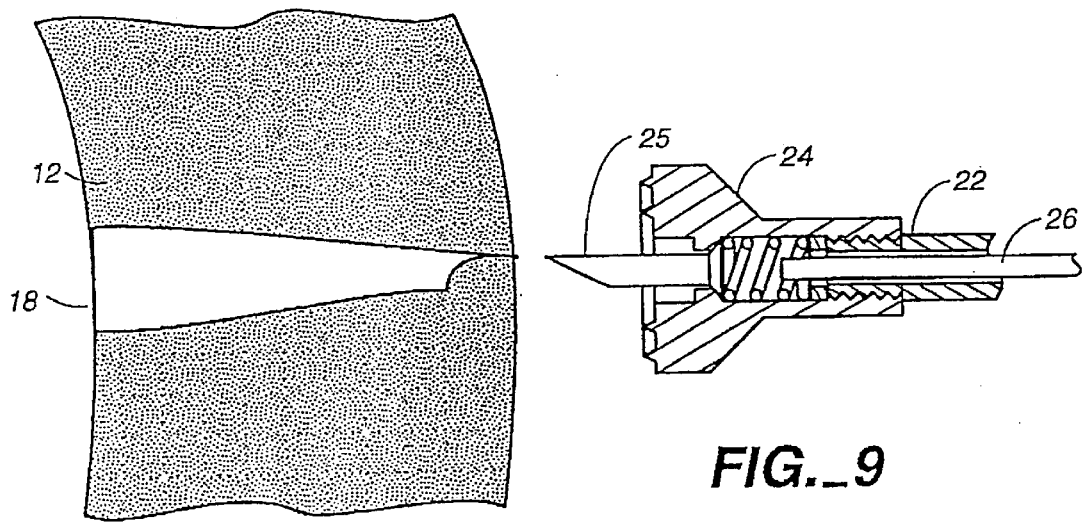
FIG._9

LASER DEVICE WITH AUTO-PIERCING TIP FOR MYOCARDIAL REVASCULARIZATION PROCEDURES

CROSS-REFERENCE TO RELATED APPLICATIONS

This application is a continuation-in-part (CIP) application of the following U.S. patent applications: U.S. patent application Ser. No. 08/628,849 filed Apr. 5, 1996, now allowed to become U.S. Pat. No. 5,738,680; U.S. patent application Ser. No. 08/675,698, filed Jul. 3, 1996, to become U.S. Pat. No. 5,766,164; U.S. patent application Ser. No. 08/664,956, filed Jun. 13, 1996, pending; U.S. patent application Ser. No. 08/794,733, filed Feb. 3, 1997 now U.S. Pat. No. 6,027,497; U.S. patent application Ser. No. 09/031,752 filed Feb. 27, 1998 now abandoned and U.S. provisional patent application 60/051,272 filed Jun. 30, 1997; which are all hereby incorporated by reference.

FIELD OF THE INVENTION

This invention relates to the field of laser surgery, and more particularly to improved laser surgery devices for use in procedures for increasing the flow of blood to heart muscle.

BACKGROUND OF THE INVENTION

Medical science has developed a wide variety of methods for counteracting the effects of cardiovascular disease including open heart and by-pass surgery. Non-surgical procedures such as percutaneous transluminal coronary angioplasty, laser angioplasty, and atherectomy have been developed.

One alternative to the aforementioned procedures is known as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1-cm deep to the epicardium. The resultant channel through the myocardium was funnel-like. A problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al. U.S. Pat. No. 5,380,316. Aita, commenting on the Hardy needle device, contends that mechanical piercing was undesirable because it entailed some degree of tearing of the pierced tissue, and that tearing often leads to fibrosis as the mechanical tear heals, a factor that severely diminishes the effectiveness of the TMR treatment. Aita, et al. also contends that exposure to metal may cause fibrosis where the needle passes through tissue. The Aita, et al. patent describes an elongated flexible lasing apparatus which is guided to an area exterior to the patient's heart and irradiates the exterior surface to form a channel through the epicardium, myocardium and endocardium. Thus, in the Aita et al. procedure, the epicardium is irradiated at a high energy density and therefore should have a large area of heart tissue removed. Consequently, the Aita et al. procedure has the same problems and disadvantages as the prior Mirhoseini TMR procedure with respect to the aforementioned bleeding problem in the outer surface of the epicardium.

In U.S. Pat. No. 5,713,894, an improved apparatus and method for TMR procedures is disclosed. In this teaching, the epicardium membrane of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed the opening that was made mechanically in the epicardium tends to close to prevent excessive bleeding from the channel formed in the myocardium. Other examples of myocardial revascularization devices with manual optical fiber advancement mechanisms include U.S. patent application Ser. No. 08/790,193 now allowed entitled "Improved Laser Device For TMR Procedures," and U.S. patent application Ser. No. 08/675,698, now allowed, entitled "Contiguous, Branched Transmyocardial Revascularization (TMR) Channel, Method & Device."

Other surgical techniques for performing TMR include U.S. patent applications Ser. No. 08/794,733 and Ser. No. 09/031,752. These disclosures teach of a viewing surgical scope apparatus that can introduce a visualization scope and a tissue ablation optical fiber for minimally invasive surgical use. These two disclosures also include a hand-held TMR optical fiber advancement and control handle assembly that attaches to an articulating handle member which in turn deflects the device's articulating distal tip assembly where the optical fiber egresses to perform the procedure. The U.S. patent application Ser. No. 08/794,733 also includes an auto-piercing mechanism in this handle assembly.

Under certain operating conditions, the characteristics of the epicardium membrane may vary so the physician may elect to use one or more different tip members on the hand-held device for carrying out the aforesaid improved TMR procedure. Also, it is desirable that the physician be able to pierce the epicardium in the most efficient manner using an auto-piercing mechanism thereby minimizing the size of the opening necessary to accommodate an advancing fiber element. The TMR device of the present invention solves these problems.

Additionally, many presently used hand-held TMR devices require manual finger control to advance the energy delivery devices such as an optical fiber while a physician fires the laser to create TMR channels. Thus, there is need for an automated TMR device.

SUMMARY OF THE INVENTION

The present invention comprises a method and apparatus for combined piercing/energy delivery myocardial revascularization of a human heart that fulfills the advantages listed below. In particular, the inventions herein are improvements to a revascularization device with handle assembly which includes a hand-held device with a mechanical piercing element for making an initial opening in the membrane of the heart. The device may include for MIS approaches an apparatus for insertion into the chest cavity of a patient. In one form, the device includes a detachable distal tip assembly including a hollow piercing means that mechanically penetrates, micro-tears or spreads the epicardium muscle fibers of the heart. The tip assembly includes a stop member for engaging the epicardium outer surface and a body portion that retains the hollow piercing member. The latter may be biased by a spring to provide a desired piercing characteristic. Within this hollow piercing member is the distal end of the energy delivery device such as an optical fiber. The hand-held TMR devices and handle assemblies include an auto-piercing mechanism for piercing the epicardium prior to revascularization procedures. The energy delivery device such as an optical fiber can be controllably displaced to pre-set displacements. Additionally, to auto-piercing, the energy delivery device can be automatically controlled by a processor, e.g. optical fiber advancement coordinated with laser firing.

After the piercing member penetrates the epicardium of the exterior wall of the heart, energy is emitted from the distal end of the energy delivery device. Thus, the myocardium and not the epicardium is treated to form a channel without treating the epicardium which can cause operative bleeding. An air suction conduit connected to the tip assembly provides means for cleaning debris from the channel being formed and keep the outer surface of the epicardium firmly against the stop member of the tip assembly. Sealing of the epicardium occurs after the piercing member of the device is removed so that a minimum of bleeding occurs after each TMR procedure.

The invention herein additionally provides alternative embodiments of a TMR hand-held device with handle assembly that includes automatic piercing in combination with automatic energy delivery device such as an optical fiber advancement sequenced with device activation for creating TMR channels. A motorized actuating mechanism is incorporated in the TMR device's handle to drive an energy delivery device such as an optical fiber and can include processor control in combination therewith.

It is therefore a general object of the present invention to provide an improved apparatus for performing myocardial revascularization for resolving the aforementioned prior devices and procedures.

A further object of the present invention is to provide a less invasive and safer device for performing myocardial revascularization which does not diminish the effectiveness of the TMR treatment and eliminates problems of excessive bleeding from a patient's epicardium following the channel forming procedure.

It is a further object of the present invention to provide an apparatus for performing myocardial revascularization which utilizes mechanical perforation or piercing of heart tissue to promote sealing of the epicardium but in such a way as to minimize the effect of any fibrosis which such perforation may cause, thereby maintaining TMR procedural effectiveness.

It is a further object of the present invention to provide an improved hand held TMR device that includes features for interchangeable and/or disposable distal tips for making an initial epicardium opening so that the TMR hand held device's control member can thereafter advance the distal end of an energy delivery device to or through the patient's myocardium.

Yet another object of the invention is to provide a device for use in a TMR procedure which uses air suction during its operation to draw blood into the channel just formed and thereby enhance the effectiveness of the procedure.

It is a further object of the present invention to provide an improved hand-held TMR device with handle assembly that includes features for automatic needle piercing by making an initial epicardium opening so that the device's energy delivery device such as an optical fiber can proceed through a patient's myocardium with coordinated activation of the energy delivery device.

It is yet a further object of the present invention to provide an improved hand-held TMR device that enables accelerated piercing by the needle member to increase peak epicardial tissue piercing capability for a physician to perform work on a heart.

It is a further object of the present invention to provide an improved hand-held TMR device that allows for one standard hand-piece design, which has interchangeable head portion designs for allowing use of various needle designs along with distal end shafting, be it a rigid shafting or a flexible catheter design, thereby enabling the creation of either straight or branched channels or the formation of stimulus injury zonal regions in myocardial tissue, and includes a safety feature that eliminates an exposed needle when not in use It is a further object of the present invention to provide an improved hand-held TMR device with handle assembly and computer based system that includes processor controlled motors within the TMR device's handle assembly for improved controllability of an energy delivery device such as optical fiber movement/firing in addition to initial auto-piercing.

Other objects, advantages and features of the present invention will be apparent to those skilled in the art from the following detailed description and the accompanying drawings.

DESCRIPTION OF DRAWINGS

FIG. 1 is a schematic view in section of a human heart showing revascularization of the myocardium utilizing a device according to the present invention.

FIG. 2 is an enlarged view in perspective showing a device embodying principles of the invention for implementing the revascularization procedure of FIG. 1.

FIG. 3 is an enlarged exploded and fragmentary view in section of the device shown in FIG. 2 showing details of the handle portion and the advancing mechanism for linear movement of a movable fiber element.

FIG. 3A is a fragmentary view in section of the distal end member for the device shown in FIG. 3.

FIG. 3B is a view in section showing an alternate form of the distal end member according to the invention.

FIG. 4 is an end view of the distal end member of the device of FIG. 3A.

FIG. 5 is an exploded view in elevation and in section of the device's distal end member of FIG.2.

FIGS. 6–9 are enlarged views in elevation and in section showing the end member of FIG. 3A assembled and in operation during a typical TMR procedure according to the invention.

DETAILED DESCRIPTION

Figure 10A:
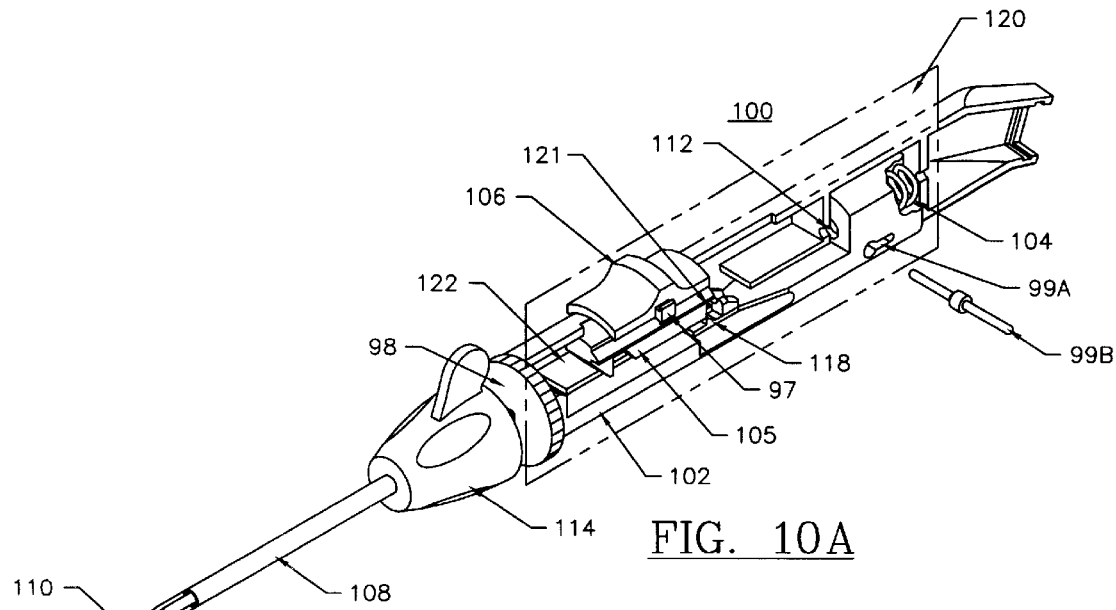
FIG. 10A is a perspective view of the auto-piercing hand-held TMR device.

With reference to the drawing, FIG. 1 diagrammatically depicts a human heart 10 with the epicardium 12 of the left ventricle 14 exposed where a myocardial revascularization procedure according to the invention is to be performed. Preliminary to the procedure the surgeon makes an incision in the patient's chest to expose the outer wall (epicardium) of the heart's left ventricle. In a human heart the wall of the left ventricle, is comprised of an outer layer, the epicardium, the main muscle thickness, the myocardium, and the inner layer or endocardium. The epicardium is comprised of a smooth, moist serous membrane which is somewhat tougher than the other tissue layers of the heart muscle.

In carrying out the method of the present invention, the surgeon utilizes a hand-held device 16 which is manipulated and operated to form a series of revascularization channels 18 in the myocardium of the patient's heart at selected spaced apart locations.

In accordance with the principles of the invention, each of channels is formed by first piercing the epicardium membrane to form a relatively small opening through which the distal end of an energy delivery device such as an optical fiber can be forced to engage the myocardium. The energy delivery device such as an optical fiber element is connected to an energy source 28, here a laser device at its proximal end. Once through this opening, laser energy is emitted from the fiber element as it is moved forwardly to form the channel in the myocardium and preferably completely through the endocardium. After the channel has been formed, the distal end of the fiber element is retracted to a position within the end member of the device 16 which can then be moved to another location to repeat the procedure. When the end member of the device is removed, the relatively small opening in the epicardium substantially closes due to the tissue resiliency, thereby minimizing any blood flow from the channel just formed. The device is connected by a flexible conduit 36 to a vacuum source 37 which helps to remove debris caused by laser action during a channel forming procedure and also to initiate blood flow into each channel as it is formed in order to maximize the revascularization process. Alternatively, this conduit 36 can provide drug delivery or irrigate the distal end of the head-piece 24.

As shown in FIG. 2, the device 16 comprises a housing 20 adapted to be hand held by the surgeon during an operative procedure, a J-shaped neck member 22 attached to the housing and an interchangeable distal head member 24 having a hollow piercing tip 25 (See FIG. 3A). An energy delivery device such as an optical fiber 26 whose proximal end is connected to the laser source 28 extends through the housing and through the neck member to the distal end member. Within the housing 20 the fiber element 26 is connected to a movable shuttle 30 (FIG. 3) which extends outside the housing and is connected to a thumb actuated control member 32. Thus, movement of the control member 32 by the surgeon will move the distal end 34 of the fiber element beyond the distal head member 24 of the neck member (FIG. 7). The vacuum line 36 extending from the vacuum source 37 such as a conventional hospital vacuum type canister device is connected to a barbed inlet 38 in the housing 20. This inlet communicates with an air passage 39 around the fiber element that extends to distal head member 24. Thus, when in use, a suction is provided at the distal head member 24 of the device 16 which performs two vital functions. First of all, the suction force draws the epicardium tissue firmly against the contacting face of the distal head member 24 so that a relatively small opening can be made in the epicardium muscle fibers to allow the distal end of the fiber element 26 to penetrate and engage the myocardium. As the fiber element is advanced by the surgeon beyond the epicardium opening and into the myocardium, laser pulses are produced from its distal end 34 to form a channel 18 through the myocardium. As the fiber element continues to advance, the air suction provided helps to remove debris caused by the laser and also draws blood into the channel to assure that the revascularization process will commence properly. When the fiber element is retracted after forming a channel, the distal end member 24 is moved away and the opening in the epicardium closes naturally with a minimum of bleeding. (FIG. 9) It will be understood that the energy device optionally may be activated to provide energy through a pilot hole formed by piercing without advancement into tissue, although such advancement is preferred.

Describing now the device 16 in greater detail, with reference to FIG. 3. The housing 20, which may be molded from a suitable plastic material, has an enlarged central cavity 40 to accommodate the shuttle 30. The latter has a cylindrical portion which surrounds and is firmly attached to the fiber element 26. Attached to the cylindrical portion is a web portion 42 which extends through an axial slot 44 in the housing. The web portion is connected to the control member 32 on the outside of the housing 20 which preferably has an arcuate configuration in cross-section with a pair of external, transverse ridge portions 46 that facilitate easy thumb control by the surgeon.

Below the central cavity 40 is the barbed inlet 38 for the vacuum line 36 which communicates with the air passage 39 to the distal end member 24. An internal rubber disk 48 is provided within the housing to seal the air passage from the central cavity 40. The disk surrounds the fiber element and is held in place along its periphery by an annular groove 49.

At its forward end, the housing tapers to a threaded end portion 50 having a tapered end surface 52 for receiving a flared end 54 of the neck member 22. With the inner surface of this flared end in contact with the tapered end surface 52, a jam nut 56 around the neck member can be tightened on the threaded end portion 50 to secure the neck member to the housing 20. The jam nut 56 is preferably provided with a radially extending, integral fin or projection 57 which provides a means for easily turning the jam nut to loosen or tighten it. This enables the surgeon to quickly adjust the axial orientation of the J-shaped neck member 22 and thus the position of the distal head member 24 relative to the housing 20.

The proximal end of the energy delivery device such as an optical fiber element 26 is connected to the source or generator 28 of laser energy which is preferably a Holmium laser that operates at a wave length in the range of 1.8 to 2.2 microns and a pulse frequency in the range of 2–25 Hertz. This type of laser is preferable because it provides high absorption efficiency, hemostosis and a moderate absorption range in myocardium tissue, and is compatible with an energy delivery device such as an optical fiber. Other laser sources that can be used are taught in U.S. patent application Ser. No. 08/729,325, filed Oct. 15, 1996, now allowed as U.S. Pat. No. 5,785,702 and U.S. patent application Ser. No. 08/904,222 now allowed, both of which are hereby incorporated by reference.

At the laser generator, laser energy is supplied to the energy delivery device such as an optical fiber 26 which, at its distal end, has a diameter of around 1 mm. The energy delivery device such as an optical fiber element is comprised of a plurality (e.g. 37) of glass fibers each having a diameter of 100 microns. These glass fibers are held together by a suitable plastic material, such a 353 ND Epoxy, and near its distal tip, the fiber element is preferably surrounded by an annular tantalum marker which serves to retain the fiber element in a closely packed geometric boundary surrounding the optical fiber element is a plastic protective sheath such as polypropelene having a wall thickness of 0.004 inches. Other fiber element configurations could be used within the scope of the invention, single fiber elements may also be used.

In the embodiment shown, the neck member 22 of the device 16 is a tubular member having a uniform outside diameter (e.g. 0.120 inches) and inside diameter (e.g. 0.094 inches) preferably bent into an angular "J" shape within which the energy delivery device such as an optical fiber element 26 is slidable. This neck portion is preferably made from a stainless steel which is heat treated to make it malleable and thus somewhat flexible. This enables the neck portion to be easily bent so that its distal end head member 24 can be positioned to accommodate the specific requirements of the surgical procedure being performed.

Removably attached to the distal end of the tubular neck is the enlarged positioning and stabilizing head member 24 for the device 16 which includes the hollow piercing tip 25 for making the initial opening in the epicardium. In the embodiment shown in FIGS. 4–9, this head member 24 has an annular flange portion with a generally planar end surface 27 that is transverse and preferably perpendicular to the axis of the inner passage and the fiber element 26 therein. One or more circular ridges 29 are provided in the end surface 27 so that the head member 24 will retain its position when pressed firmly against the epicardium of the heart.

The hollow tip member 25, preferably made of a suitable metal, e.g. stainless steel, has an inner diameter that is sufficient to accommodate the fiber element 26 with ample clearance so that the latter will slide freely through it. At its distal end the tip member is beveled to form a sharp anti-coring needle point 58. At its other end, the tip member has an enlarged tapered head portion 60.

The distal head member 24 has a body portion 62 with an enlarged central bore 64 having internal threads 66 that enables it to be quickly attached to the end of the neck member. In lieu of the threads 66, the head member 24 could be connected to the distal end of the neck member 22 by means of a Luer taper and lock nut combination (not shown) which is a standard connection system for tubular parts that is well known in the medical field.

Within one end of the bore 64 is an annular conical seat 68 which supports the enlarged head portion 60 of the tip member 25. A coiled spring 70 is preferably provided within the central bore to contact the enlarged head of the tip member and urge it against the seat 68. However, if a level of resistance is encountered by the tip member during its initial contact with the epicardium, the spring will allow some retraction of the tip member, thereby easing the initial penetration process.

An alternative form of head end member 24a according to the invention is shown in FIG. 3B. In this embodiment the removable piercing tip member 25 is protected by a movable outer sleeve member 72 that functions as a shield means and has a flared portion 74 with an end surface 76 that contacts the epicardium surface. The outer sleeve member is co-axial with and movable relative to an inner sleeve member 78 having an enlarged inner end portion 80. This inner sleeve has a central bore with internal threads 82 at its inner end to facilitate its connection with the distal end of the J-shaped neck member 22. Within the bore is an annular tapered surface 84 that forms a seat for the tapered head end of the piercing tip member 25. At the outer end of the inner sleeve member is an annular flange portion 86 which extends radially within an elongated inner slot 88 in the outer sleeve member 72. Similarly, at the inner end of the outer sleeve member is an inner end flange 90 that extends inwardly within an extended slot 92 that is formed by the end flanges 80 and 86 of the inner sleeve 78. Situated within the extended slot 92 is a coiled spring 94. When the head end member 24a is not in use and no axial force is applied against the end surface 76, the outer sleeve, 72, urged by the spring 94 extends beyond the end of the tip member 25 and thus protects it from any inadvertent contact with any surrounding object. When in use, as the end surface 76 of the outer sleeve is placed against the epicardium surface, it is moved rearwardly against the spring 94 so that tip member 25 can proceed to pierce the epicardium membrane in the desired manner.

The length of the tip member 25 is such that, in the embodiment of FIG. 3A, its tapered end normally extends around 0.2 inches beyond the contacting surface 27 of the head member 24. Similarly, in the embodiment of FIG. 3B, when the outer sleeve 72 is retracted against the spring 94, the tip member can project the same distance so that it will penetrate well through the epicardium in actual use. However, tip members of varying lengths may be used interchangeably by the surgeon to accommodate different conditions in accordance with the invention.

The use of the device 16 in a Transmyocardial Revascularization (TMR) procedure according to the invention is illustrated in FIG. 1 and in greater detail in FIGS. 6–9. After the surgeon makes an opening in the patient's chest to expose the left ventricle outer wall of the heart, the device 16, connected to its laser source is held by the surgeon.

During the TMR procedure the device 16 is maneuvered so that its head end 24 is placed against the epicardium of the left ventricle. (FIG. 6) The annular end face 27 of the head end member 24 serves as a stop as it is pressed against the outer surface of patient's heart. As this is done, the piercing tip member 25 first penetrates the tougher outer epicardium layer of the heart muscle while the distal end of the fiber element 26 is just inside the piercing member. The spring 70 provides a cushioning effect as the piercing member first engages the epicardium surface. With the head end member 24 in place and the piercing member 25 through the epicardium, the fiber element 26 is moved forward from the distal end of the device as shown in FIG. 7 by movement of the control knob 32 as laser pulses are simultaneously transmitted from its distal end 34. As laser energy is emitted, the distal end of the energy delivery device such as an optical fiber element proceeds through the myocardium portion of the ventricle wall 12 and ultimately through the inner endocardium layer. (FIG. 8) As the fiber element advances and pulses laser energy it forms an expanding channel 18 in the myocardium that provides the revascularization of the heart muscle.

An important feature relative to the present invention is that the epicardium is pierced or penetrated mechanically but is not subjected to laser energy. The piercing tip member 25 penetrates through the epicardium with only a minimal damage to tissue and while protecting the distal end of the fiber element 26. Thus, after the channel 18 is fully formed, the fiber element 26 is retracted by the control knob 50 and the piercing member 25 is removed. (FIG. 9) The opening caused by the piercing member normally closes due to the resiliency of the muscle fibers in the epicardium so that there is no bleeding or only minimal bleeding on the outer surface of the heart. From the forgoing it is apparent that the present invention provides an improved device for performing TMR procedures that affords versatility by virtue of its removable, replaceable distal tip members 25 and which enables the formation of effective channels for revascularization that normally close at the epicardium membrane to minimize post-operative bleeding.

AUTO-PIERCING ADVANCE MECHANISM USING MANUAL CONTROL

Figure 10B:
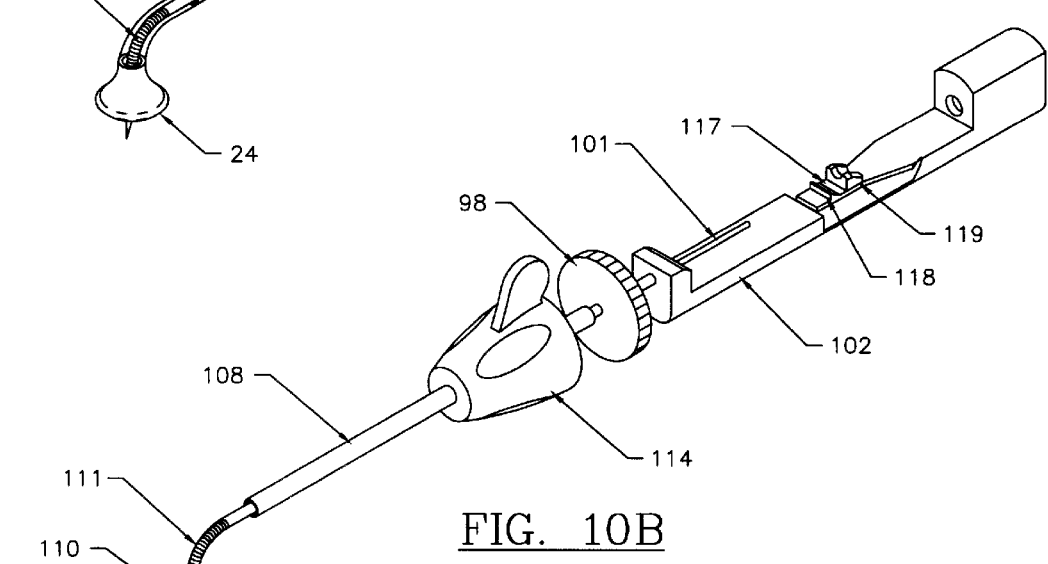
FIG. 10B is a perspective view of portions of the device shown in FIG. 10A.
Figure 10C:
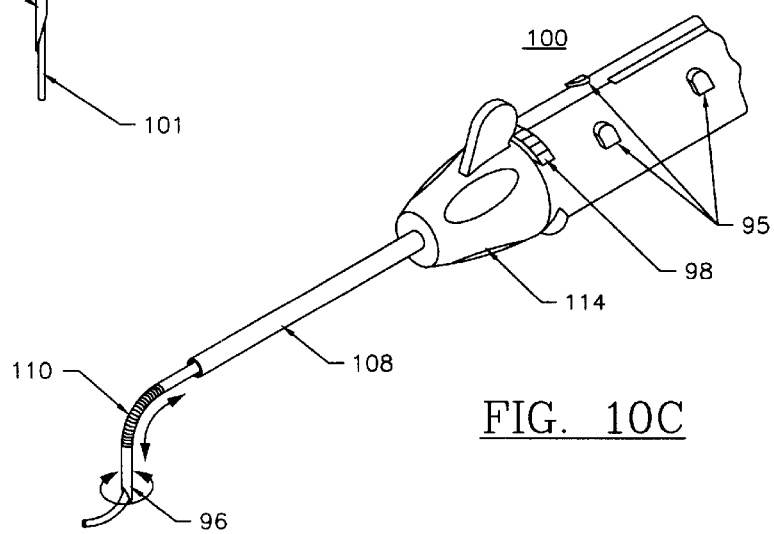
FIG. 10C is a perspective view of the outer housing portions of the hand held device shown in FIG. 10A showing the depth stop features and the kinematics of the piercing needle.

FIGS. 10A–10C show in a partial perspective view an auto-piercing hand held TMR device 100 with an energy delivery device such as an optical fiber 101 that is preferably insertable therein. The device 100 includes a piercing needle trigger slide 102 that attaches to the flexible piercing needle tube 110, a slot 112 for passage of the fiber element 101 there-through to the device's distal head member section. The mechanical auto-piercing assembly 120 of the device 100 includes the device's 100 housing which has an integral slider flange 122 attached thereto for guiding an actuator slide 105, a trigger slide 102 with a biasing spring 104 and an actuator slide member 105 which attaches to the finger slide 106. An optional pin locking member 99a & 99b can be included with the assembly 120 to lock the motion of the trigger slide 102 in place and prevent accidental trigger release. The trigger slide 102 is typically made of a plastic material such as delrin. The trigger slide 102 has a flexible tongue section 117 which allows the trigger/release action of the assembly 120. The actuator slide 105 attaches to a finger slide 106 which is finger controlled by a physician. The finger slide 106 provides both auto-piercing actuation and energy delivery device such as an optical fiber advance control for precise, one-handed advance and withdrawal of the energy delivery device such as an optical fiber element 101 during TMR treatment. This hand device 100 has a tip rotation control knob 114 which allows 360 degree tip rotation control for accessing all areas of a heart, including the posterior wall of the left ventricle. The outer guide tube shafting 108 is typically a malleable tube and can be shaped for precise positioning and control of the tip end member 24. The hand-held device's 100 handle includes pre-set fiber optic depth stops 95 formed integral with the device's 100 external housing as shown in FIG. 10C. The handle member's slider 106 has a cross-slide member 97 within which can engage these depth stops 95 to limit advancement of the energy delivery device such as an optical fiber 101. The depth stops 95 as shown typically limit external advancement of the energy delivery device such as an optical fiber 101 distal to the outer guide shafting 108 to 2.5 cm, 3.0 cm and 3.5 cm extension there beyond to accommodate varying myocardial wall thickness. The piercing needle flex tube 110 can rotate and advance simultaneously at the distal end of the outer guide shafting 108 if required. The piercing needle's 110 flexible bending section 111 has various cuts, slits and perforations in the semi-rigid material and/or an interposed flexible tubing member which allows for these types of motions. As shown, the bend 111 is formed by a helical cut in the piercing needle tube 110. The control knob 98 allows the distal end of tube 110 to be rotated thereby allowing the formation of branched channels in myocardial tissue by using a structural guiding member at the distal end of tube 110 and shown as feature 96. Alternatively, the flexible needle may be constructed of an elastomer material.

FIGS. 11A–11G are side views of the mechanical auto-piercing assembly 120 that form part of the hand held device shown in FIG. 10A which representatively shows the operational timing sequence of the auto-piercing assembly 120.

Figure 11A:
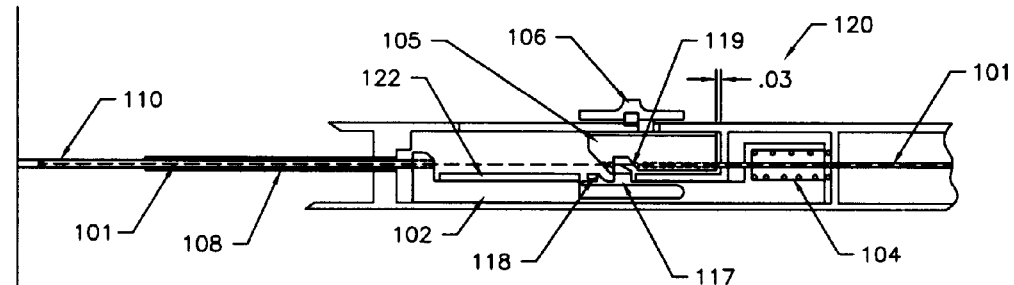
FIGS. 11A, 11B, 11C, 11D, 11E, 11F & 11G are side views of the mechanical auto-piercing assembly that form part of the hand held device shown in FIG. 10A which show the time sequence of operation.

FIG. 11A shows the finger slide retracted to its almost maximum end of travel of the finger slide 106 and ready for use in a triggered condition. The piercing needle 110 is representatively shown at a datum surface such as a heart's epicardial surface. The 0.03 indicates the advanced free space between the end of the actuator slide 105 within the device's 100 housing. The datum surface is representative of an epicardial surface. The actuator slide 105 has a beveled slider face 119, and the trigger slide 102, which has a catch element 118, retains the slider 102 in place prior to forward movement caused by biasing spring 104.

Figure 11B:
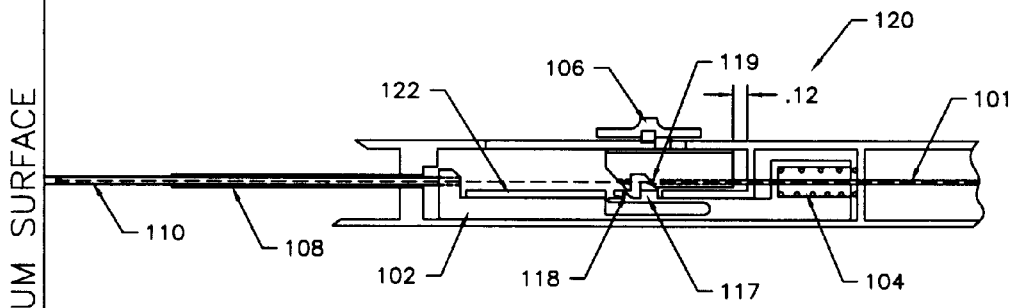

FIG. 11B shows the finger slide 106 slightly advanced to a 0.12 relative advanced position and the beginning of a trigger release event of the trigger slide 102. The slider face 119 engages a corresponding face on the trigger slide 102 causing the tongue member 117 to begin to depress which in turn causes the catch element 118 to begin the trigger release event.

Figure 11C:
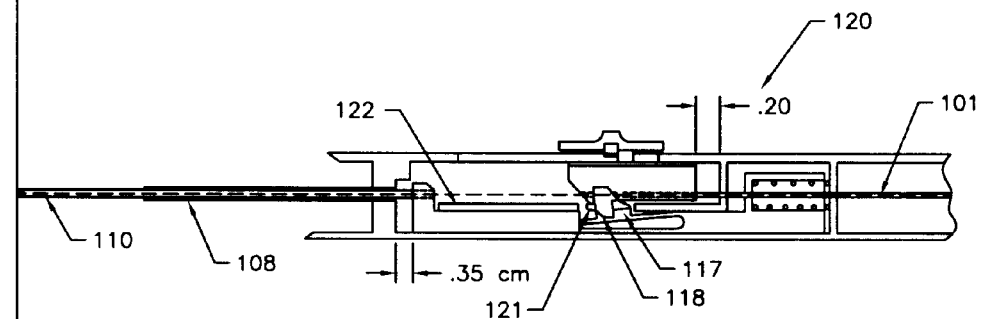

FIG. 11C shows the finger slide 106 further advanced to a 0.20 relative advanced position and the onset of the trigger release event of the trigger slide 102. The slider face 119 slides and depresses the corresponding face on the trigger slide 102 causing the tongue member 117 to depress to the point where the catch element 118 is disengaged from a retention flange that forms part of the housing, releasing the trigger slide 102 causing the piercing needle 110 to begin epicardial tissue penetration.

Figure 11D:
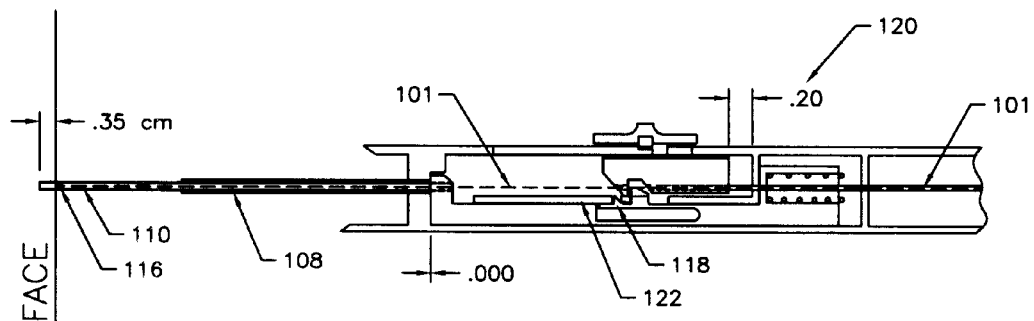

FIG. 11D shows the finger slide at the 0.20 relative advanced position of the finger slide 106 and the trigger slide 102 at the end of the housing which is displaced by 0.35 cm, i.e. the penetration depth of the piercing needle 110 into myocardial tissue. The distal end 116 of the energy delivery device such as an optical fiber element 101 is ready to commence lasing action to ablate myocardial tissue.

Figure 11E:
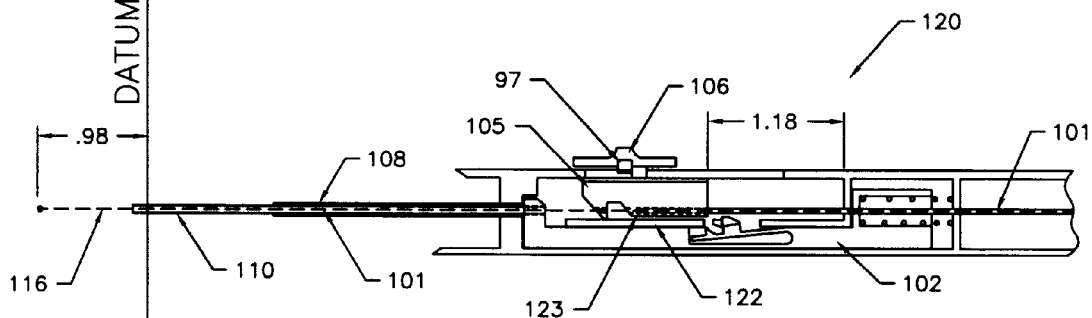
Figure 11F:
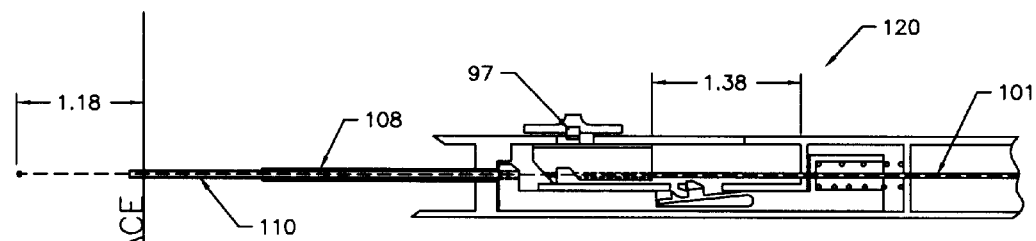
Figure 11G:
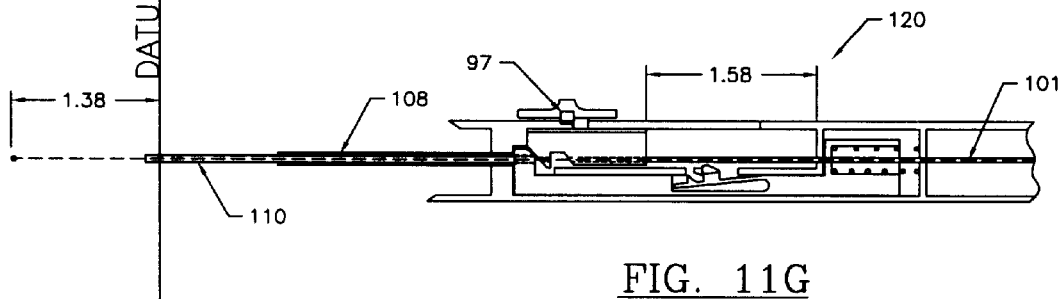

FIG. 11E–11G show the finger slide 106 at a 1.18, 1.38 & 1.58, respectively, relative advanced positions which causes the energy delivery device such as an optical fiber's distal end 116 to advance to a 0.98 (typically 2.5 cm), 1.18 (typically 3.0 cm) and 1.38 (typically 3.5 cm) relative positioning using a first, second and third fiber advance position in myocardial tissue, e.g. using the depth stop feature 95. The device's 100 housing as shown in FIG. 10C has these depth stop 95 members which cooperatively engage cross member 97 in the finger slide 106.

In U.S. patent application Ser. No. 08/675,698, now allowed as U.S. Pat. No. 5,766,164, entitled "Contiguous, Branched TMR Channel, Method and Device," a hand-piece rotational mechanism causes a hollow curved piercing needle with the above discussed guiding structural feature 96 shown in FIG. 10C to rotate 180 degrees with respect to the central axis of an actuating gear mechanism. The needle rotates within its original pierced hole to indexed positions, producing branched TMR channels from a single entry epicardial entry point. The embodiments discussed below of a TMR device with handle assembly in FIGS. 12A–12G can also be an auto-piercing needle device using a motor for branched channel formation.

AUTO-PIERCING ADVANCE MECHANISM USING MOTORIZED CONTROL

FIGS. 12A, 12B, 12C, 12D, 12E, 12F & 12G are perspective views in broken view of motor assist auto-piercing needle assemblies showing various embodiments of a hand held TMR device 130. These embodiments include a piercing needle mechanism for producing TMR channels with respect to the piercing axis of a TMR device's head tip portion. In particular, the mechanical translational motion of a piercing needle is accomplished by various mechanical mechanisms with optional rotation of the piercing needle for branched channel formation. The FIGS. 12A–12G show the hand-held TMR device 130 with handle assembly with thumbwheel 140 that is used to actuate the piercing needle using either a motor or manual drive mechanism. The side knob 128 provides depth stop control of the energy delivery device such as an optical fiber to preset displacements, e.g. 2.5, 3.0 & 3.5 cm. The thumbwheel 140 can be a control mechanism for an electric drive motor discussed in FIG. 14 below.

Figure 12A:
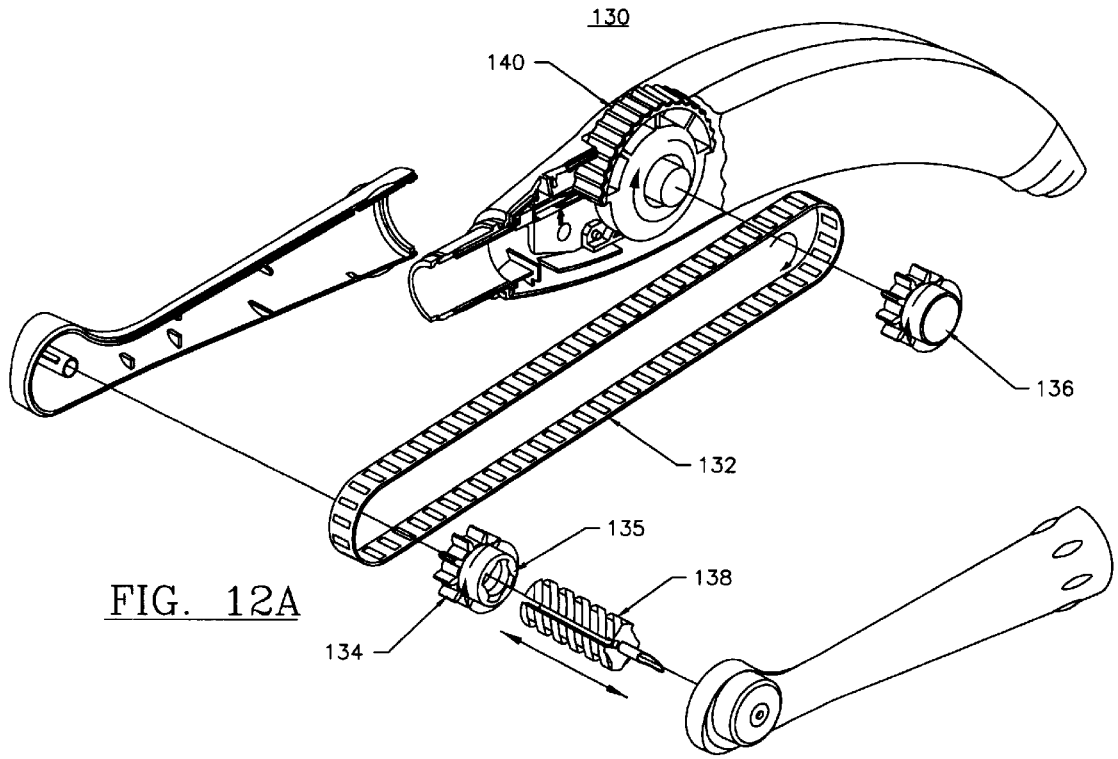
FIGS. 12A, 12B, 12C, 12D, 12E, 12F & 12G are perspective views of a motor assist auto-piercing assembly for various hand held TMR devices.

FIG. 12A shows a belt driven gear mechanism using two pinion gears 134 & 136 wherein the device's proximal gear 136 attaches to the thumbwheel 140 or optionally a drive motor mounted within the device 130 housing, and a distal pinion gear 134 which causes reciprocation of a piercing needle 138 lead screw. This belt mechanism is located inside the front molded pivot/swivel section of the hand-piece 130. When the proximal pinion gear is actuated by a motor within the handle portion of the device 130, the belt 132 rotates distal pinion gear 134 causing the rotation and advancement or retraction of the piercing needle 138.

Figure 12B:
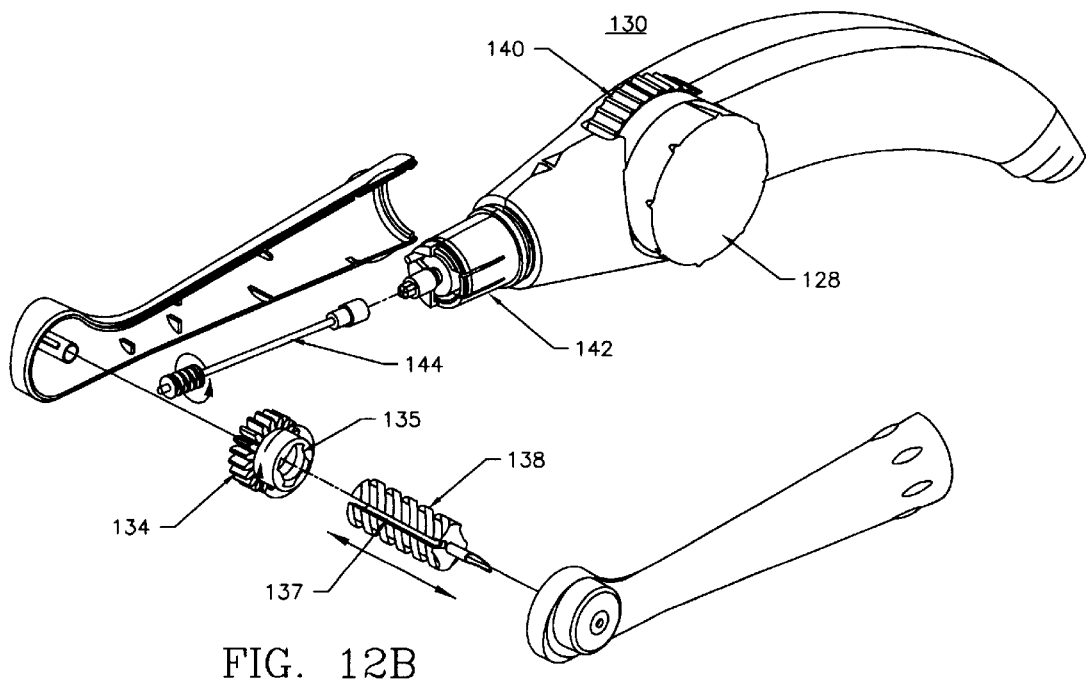
Figure 12C:
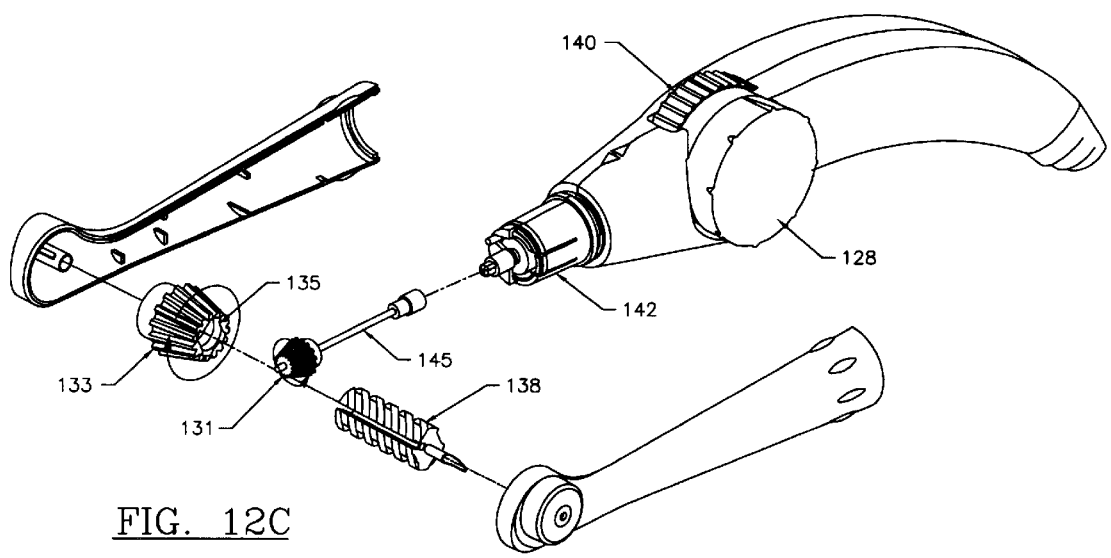

FIG. 12B–12C show worm and bevel gear mechanisms respectively for rotating and reciprocating a lead screw piercing needle 138. The lead screw 138 is typically keyed to a slot 137 for preventing needle 138 rotation. Removal of the key causes the needle 138 to rotate. FIG. 12C shows a straight head portion section with a retractable piercing needle member 138 using a first bevel gear 131 which is driven by a drive shaft 145 which is rotated by a motor 142. The first bevel gear 131 meshes with a second offset bevel gear 133 supported by structural members within the housing. The piercing needle member 138 translates by a second bevel gear 133 via lead screw threads on the outer portions of the piercing needle member 138 which mesh with internal threads 135 of the second bevel gear 133. The lead screw of the piercing needle 138 can be keyed to prevent rotation of the needle member 138 when translating. If such a locking key is removed, the needle member 138 can rotate and enable the ability to create branched channels when the distal end of the needle member 138 includes a guiding structure for directing the energy delivery device such as an optical fiber as similarly taught in U.S. patent application Ser. No. 08/675,698 as discussed above.

Figure 12D:
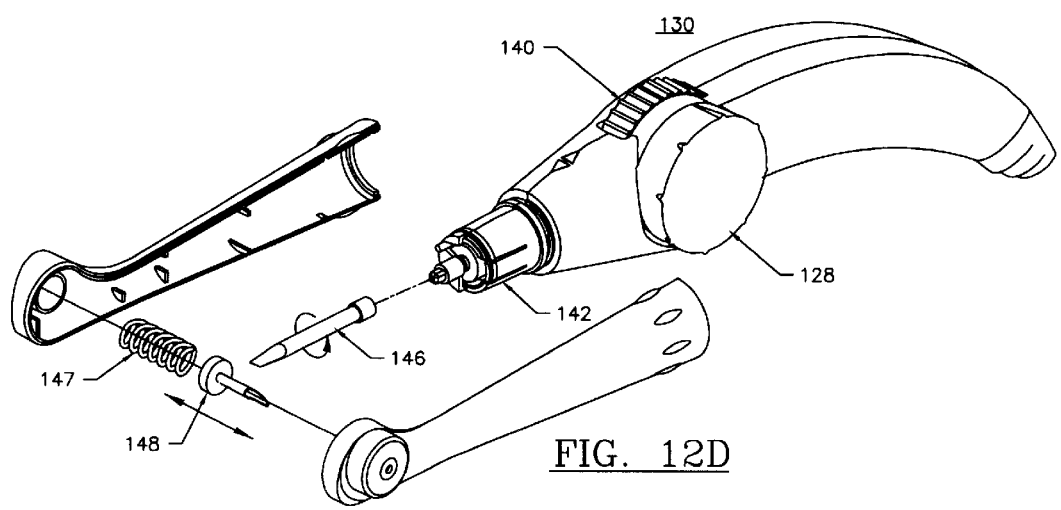

FIG. 12D shows a straight head portion section with a retractable piercing needle member 148 using a rotating shaft 146 with a bladed end portion that lifts and lowers the piercing needle 148 with required advancement/retraction. The actuator is a motor 142 which drives the shaft 146 whose distal end with a screwdriver shaped blade cooperatively causes a spring 147 which biases the piercing needle member 148 and is retained within a molded socket of the hand-piece's arm. When the shaft 146 rotates, the piercing needle 148 either advances/retracts from the housing.

Figure 12E:
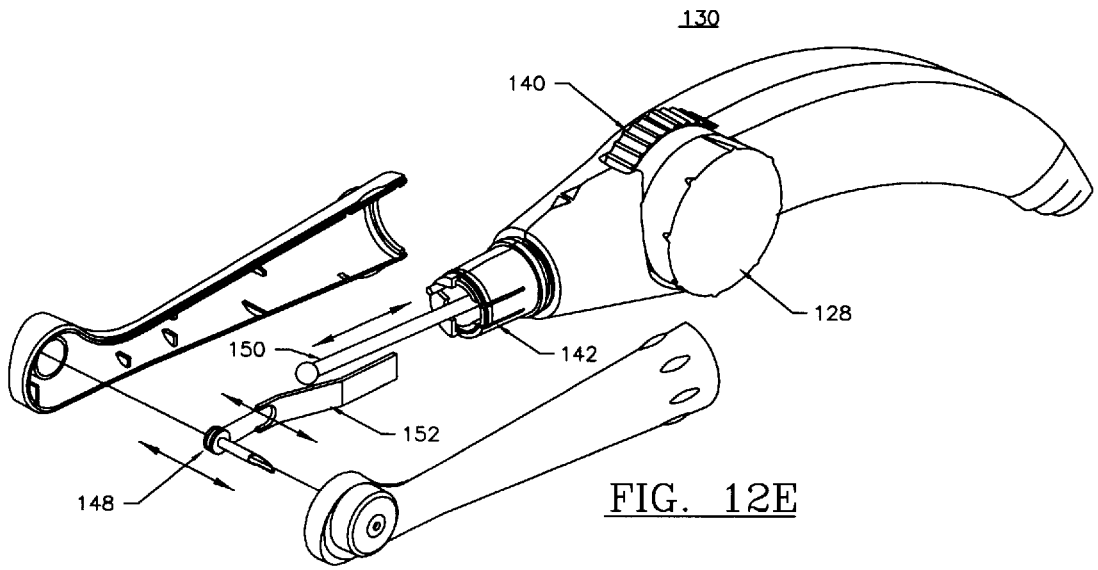

FIG. 12E shows a straight head portion section with a retractable piercing needle member 148 using a leaf spring biasing member 152 attached to the piercing needle 148 along with an actuator member 150 that translates in and out of the housing using a linear motor 142. The actuator member 150 depresses the leaf spring member 152 causing linear reciprocating member to move longitudinally in and out of the hand-piece 130. A fixed end of leaf spring 152 attaches inside a front molded portion of the hand-piece. When this pre-shaped leaf spring 152 is depressed by actuator member 150, the piercing needle 148 advances or retracts from the device's housing.

Figure 12F:
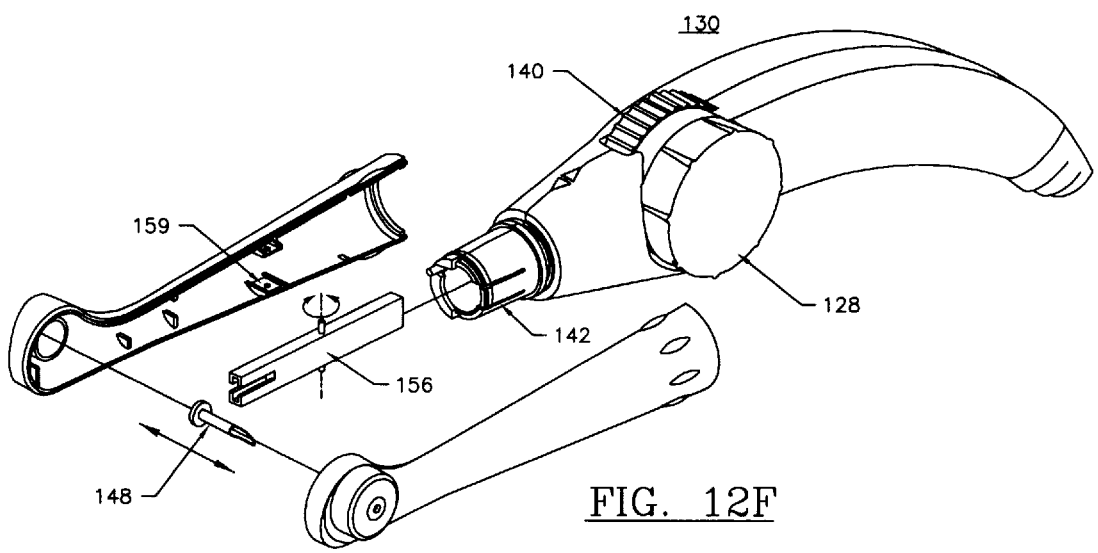
Figure 12G:
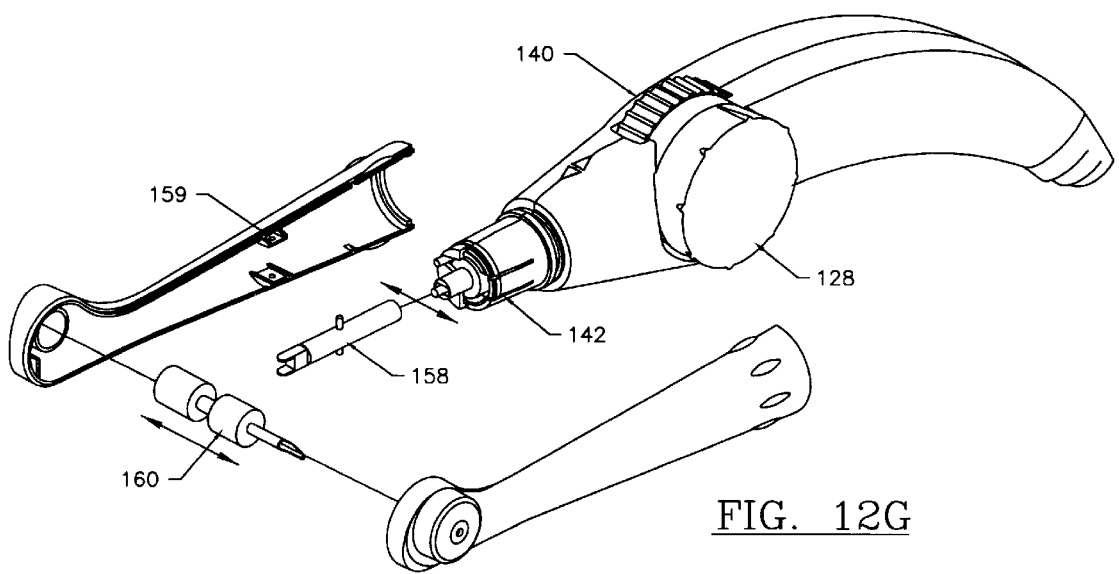

FIGS. 12F & 12G show a straight head portion section with a retractable piercing needle member 148 and 160 using a pivotal arm 156 & 158 that is actuated by a motor 142, pivoting of the arm 156 & 158 causes the advancement or retraction of the needle member 148 & 160 respectively. The pivotal arm is retained in sockets 159 of the housing. If the needle is required to rotate for creating branched channels, the pivot arm's 156 internal slot for retaining the needle 148 can include a rack and pinion mechanism with a gear element attached to the top of the piercing needle 148 for needle rotation and the housing motor can include a driver for longitudinal movements within the hand-piece's outer arm section.

Figure 13:
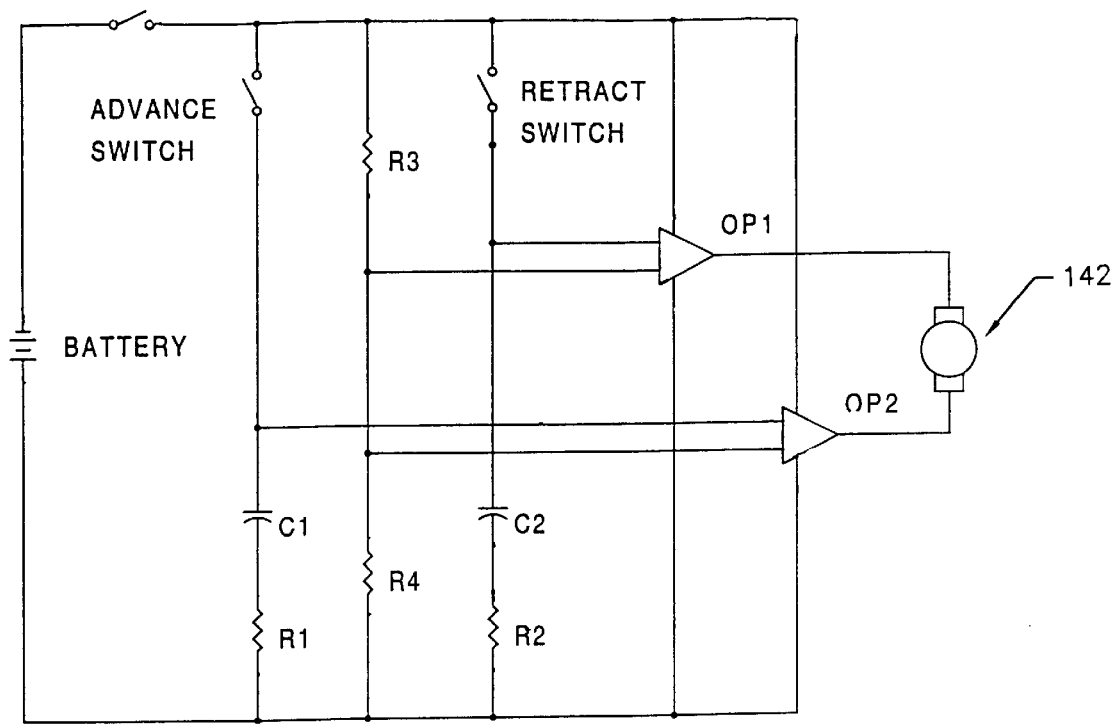
FIG. 13 shows an electrical schematic for a motor operated hand-held device for any of the embodiments shown in FIGS. 12A–12G.

FIG. 13 shows an exemplary electrical schematic of a motor controller for controlling motor 142 that advances or retracts the piercing needle member shown in FIGS. 12A–12G. This controller is direct current (DC) powered and includes three switches for control of the piercing needle element. A power-on switch provides power to the controller, and an advancement and a retraction switch are used for controlling the rotation of the motor. The advancement/retraction microswitches which mechanically interlink with thumbwheel 140.

AUTO-FIBER ADVANCE USING PROCESSOR CONTROL

U.S. patent application Ser. No. 08/664,956, entitled "Interoperative Myocardial Device and Stimulation Procedure," teaches of a method for creating stimulus revascularization zones in myocardial tissue in the heart's ventricular wall is taught. This disclosure teaches of a method which includes steps for moving a distal end of an energy delivery device such as an optical fiber element forwardly through the heart's epicardium into myocardial tissue by firing laser energy from the fiber's distal end to form stimulus injury zones that promote capillary growth and tissue revascularization. A TMR hand-held device as taught therein includes auto-fiber advance with sequenced laser firing. The types of optical fibers used include various optical fiber tip designs to create stimulation zones within myocardial tissue. The devices taught herein can include these various optical fiber tip designs to create these stimulation zonal regions.

Figure 14:
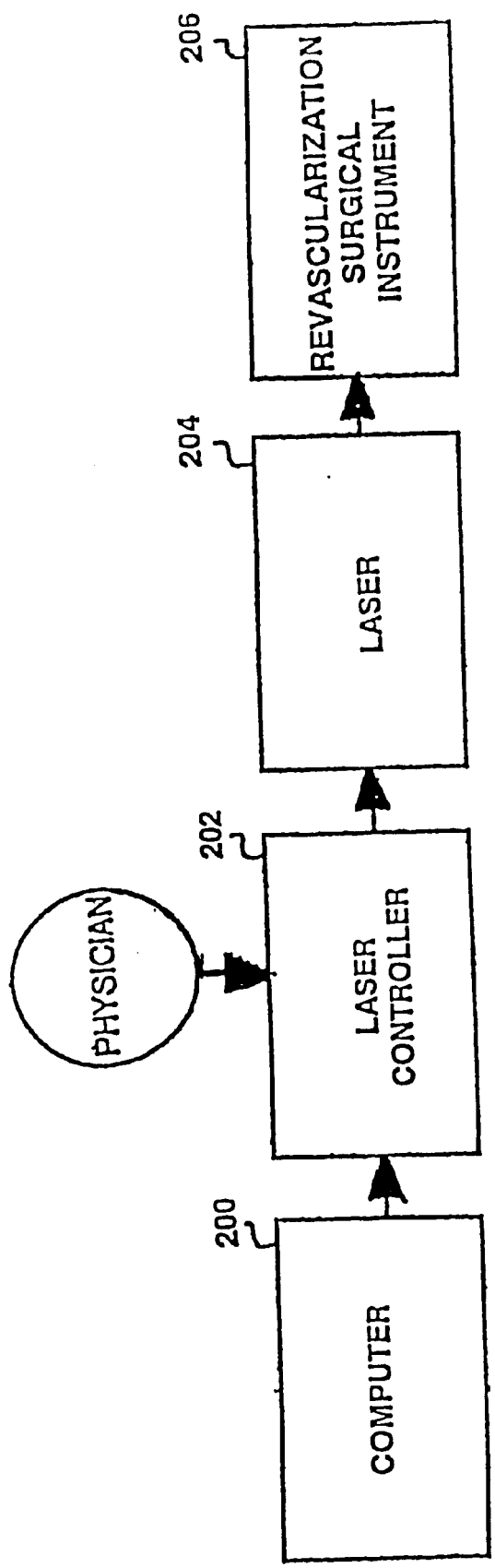
FIG. 14 shows a block diagram showing the control scheme for an automatic piercing needle with auto-fiber advance within the hand held TMR device.
Figure 15:
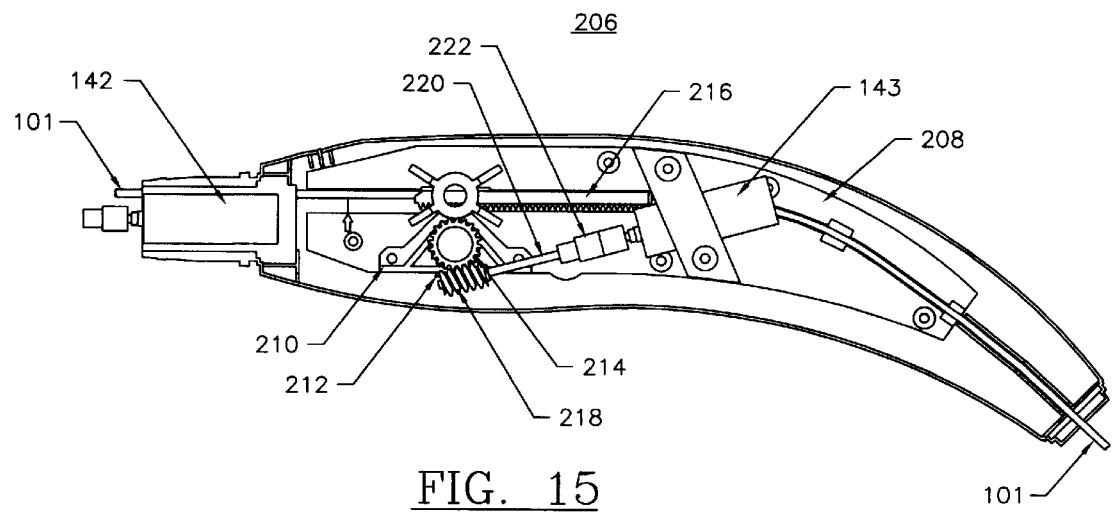
FIG. 15 shows a side view of the handle assembly with an auto-piercing needle motor and auto-fiber advance mechanisms that can be incorporated with any of the TMR devices with handle assemblies shown in FIGS 12A–G.

FIGS. 14–15 combined represent a control scheme and device for auto-piercing with auto-fiber advance. The hand held device 206 can include any of the auto-piercing needle mechanisms shown in FIGS. 12A–12G as discussed above and auto-fiber advancement as discussed below and representatively shown in FIG. 15. In particular, the hand-held device 206 with auto-fiber advancement and laser firing creates consistent TMR channels. The computer 200 via laser controller 202 can enable or disable laser firing, alter laser energy, command fiber advancement via the advancement mechanisms shown in FIG. 15, and/or control the pulse rate based upon observed tissue penetration. The computer 200 functionally: a) causes initial auto-piercing by a hand-held device prior to fiber advancement; b) automatically fires the laser followed by controlled advancement prior to next laser firing, c) allows deviation of the pulse repetition rate to adjust channel formation characteristics and minimize lateral tissue damage effects and d) allows most of the laser pulse energy as a function of channel depth for enhanced channel formation. The computer 200 and hand-piece includes a manual override feature which allows a physician manual control. Laser parameters for TMR are taught in U.S. patent application Ser. No. 08/729,325 entitled "Method for Non-Synchronous Laser-Assisted TMR", now allowed, as discussed above. The computer 200 operates in real-time to fire the laser 204 through proper control signals to the laser controller 202. The laser controller 202 also controls the laser parameters based upon previously stored a-priori condition(s) according to preferred channel formation parameters in computer 200. The optical fiber advancement rate is dependent on the energy level and rate delivered to achieve desired tissue ablation. Computer 200 also automatically actuates the auto-piercing mechanisms as discussed above in FIGS. 12A–12G using the motor 142. Energy from the laser 204 is optically transmitted to a distal end of the surgical instrument's 206 fiber tip whereupon heart tissue vaporizes creating a TMR channel. One or more pulses of laser irradiation can be used to create the TMR channel resulting in left ventricle penetration. During a TMR procedure, the fiber distal tip is preferably offset from a tissue surface undergoing treatment by about 0.25 mm prior to each laser pulse firing. Alternatively, the optical fiber can be urged against tissue in a compressed state prior to each laser pulse firing. The computer 200 controls this proper sequence of needle piercing along with fiber advancement and laser firing. The fiber advancement mechanism is preferably driven by a stepper motor 143. Alternatively, the motor 143 for fiber advancement can physically be located in a distal laser controller housing with a conduit for advancing the energy delivery device such as an optical fiber through a hand-held device or the housing can include a flexible drive shaft which drives a gear mechanism within a hand-held device to advance an energy delivery device such as an optical fiber. The computer 200 can be a processor incorporated within the handpiece and be battery operated. FIG. 15 shows the internal components for auto-fiber advance in a TMR hand-piece 206. The TMR device 206 shows auto-fiber motor 143 which preferably is a stepper motor with an auto-piercing mechanism shown in FIGS. 12A–12G. A drive shaft 220 with worm gear 218 attached thereto drives a pinion gear 212 which in turn advances/retracts a rack member 216. The optical fiber 101 in turn is driven by a rack member 216. A slip coupling clutch 222 is included with a motor drive shaft 220 for motor protection. A mounting bracket 210 supports the driven assembly 214. This bracket 210 is mounted within the TMR handle's backing plate 208. Alternative motive forms to advance or retract the energy delivery device such as an optical fiber include pneumatic or fluid motors with appropriate tubing and valving components for the control thereof.

Any of the above TMR hand devices with handle assemblies described in FIGS. 10–15 above can include evacuation/irrigation/drug delivery ports and delivery components at the head member 24 with associated tubular members within the hand-held TMR device that is connectable to a vacuum source as shown in simplified form in FIG. 1 herein which draws heart tissue against a distal contact surface of the head member 24 and can also assist in removal of ablated tissue and draw blood into the TMR channel.

Additionally, the TMR devices with handle assemblies discussed above can include an optical fiber with piercing tip element as taught in U.S. Pat. No. 5,703,985 and U.S. patent application Ser. No. 08/995,963 filed Dec. 22, 1997. Such piercing fiber tip designs obviate the need for a piercing tip member 110 in the above hand-held TMR devices. The optical fiber with a piercing tip as taught by these two disclosures can be attached to the auto-piercing and fiber advance mechanism shown in FIG. 15 where the motor 142 can be eliminated.

In U.S. patent applications Ser. No. 08/794,733 now U.S. Pat. No. 6,027,497 and Ser. No. 09/031,752, now abandoned the viewing surgical scope includes at least the visualization scope and a laser energy delivery device such as an optical fiber for use in a minimally invasive surgical TMR procedure. These two patent disclosures teach of hand-held TMR optical fiber advancement and control handle assembly that forms part of an articulating handle member for control of the device's articulating distal tip assembly. The U.S. patent application Ser. No. 08/794,733 includes an auto-piercing mechanism in this handle assembly for causing auto-piercing in relation to optical fiber advancement. These surgical viewing scope apparatus can be either a bronchoscope or endoscope in combination with a laser optical fiber that are introduced through a minimally invasive formed penetration in a patient's chest. Any of the hand-held TMR devices with handle assemblies shown in FIGS. 10–15 can be used with this prior invention's minimally invasive surgical TMR handle assembly.

Finally, the optical laser energy device disposed within a lumen defining structure of the housing can be interchanged with other channel forming device such as fluid jet, R-F electrodes or mechanical parting/piercing components that may require an auto-piercing mechanism as presented herein for initial epicardial penetration prior to tissue removal.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

We claim:

1. A hand held auto-piercing mechanism comprising:

a handle assembly having a head portion whose distal end is configured to engage tissue;

a channel forming device extending through the handle assembly and head portion, the channel forming device comprising an optical fiber;

a piercing means surrounding the channel forming device for making an initial opening in tissue, the piercing means includes a piercing tubular member which is retractable into the head portion, the piercing tubular member has a tapered tip portion and an internal bore for allowing slidable displacement of the optical fiber, a distal section of the piercing tubular member includes a means for axially bending of the piercing tubular member, and the optical fiber therein; and a movement means operatively attached to the piercing means and the channel forming device for independently controlling the movement of the piercing means and the channel forming device, the movement means comprises an adjustment means for moving the optical fiber within the handle assembly and head portion, the adjustment means forms part of the handle assembly, whereby the optical fiber's distal end can move beyond the head portion, and a means for presetting displacement of the optical fiber, thereby limiting the optical fiber's displacements.

wherein the piercing means is wholly responsive to the movement means for making an initial opening in tissue.

2. The device of claim 1 wherein the handle assembly further includes rotational adjusting means for orienting the tapered tip portion, the rotational adjusting means attaches to the piercing tubular member and the handle assembly, the piercing means further includes a means for offsetting an angle of the optical fiber from the piercing means.

3. The device of claim 1 wherein the adjustment means includes a movable shuttle which connects to the optical fiber and moves independently and inter-lockingly with the movement of the piercing means.

4. The device of claim 1 wherein the adjustment means for moving the optical fiber includes a means for operably advancing the optical fiber at a rate coordinated with a configurable laser energy source.

5. A hand held auto-piercing mechanism comprising:

a handle assembly having a head portion whose distal end is configured to engage tissue;

a channel forming device extending through the handle assembly and head portion;

a piercing means surrounding the channel forming device for making an initial opening in tissue; and a movement means operatively attached to the piercing means and the channel forming device for independently controlling the movement of the piercing means and the channel forming device, the movement means comprising a controlling means for controllably advancing the channel forming device at a rate coordinated with a laser energy source, wherein the piercing means is wholly responsive to the movement means for making an initial opening in tissue.

6. A surgical device for treating myocardium comprising:

a handle assembly with a distal end configured to engage epicardium including at least one distal opening communicating through the hand assembly;

a piercing mechanism within the distal end of the handle assembly, movement of said piercing mechanism relative to and translatable through said opening;

a substance delivery conduit distally connected to the handle assembly through to the opening and proximally connected to a source; and an acceleration mechanism operatively coupled to the handle assembly for controllably advancing the piercing mechanism through the opening and epicardium to myocardium;

wherein the piercing mechanism is wholly responsive to the acceleration mechanism.

7. A hand held auto-piercing mechanism comprising:

a handle assembly having a head portion whose distal end is configured to engage tissue;

a channel forming device extending through the handle assembly and head portion;

a piercing means surrounding the channel forming device for making an initial opening in tissue; and a movement means operatively attached to the piercing means and the channel forming device for independently controlling the movement of the piercing means and the channel forming device, the movement means further comprising an actuating means, wherein the piercing means is wholly responsive to the movement means for making an initial opening in tissue and operation of the actuating means triggers a spontaneous advancement of the piercing means.

8. The device of claim 7 wherein the actuating means comprises an actuator, a trigger, and a biasing member, the actuator operatively attached to the trigger and holding the trigger in place, the biasing member operatively attached to the trigger and initially having potential energy prior to operation of actuator, wherein operation of the actuator results in a trigger event, the trigger event initially resulting in the disengagement of the actuator from the trigger, whereby the biasing member causes the spontaneous advancement of the piercing means.

9. The device of claim 7 wherein the handle assembly further comprises a depth stop, wherein, during displacement, the depth of the channel forming device in tissue can be controlled.

10. A hand held auto-piercing mechanism comprising:

a handle assembly having a head portion whose distal end is configured to engage tissue;

a channel forming device extending through the handle assembly and head portion;

a piercing means surrounding the channel forming device for making an initial opening in tissue; and a movement means operatively attached to the piercing means and the channel forming device for independently controlling the movement of the piercing means and the channel forming device, the movement means further comprising an actuating means, wherein the piercing means is wholly responsive to the movement means for making an initial opening in tissue and operation of the actuating means results in a first event followed by a second event, the first event resulting in a spontaneous advancement of the piercing means, the channel forming device remaining at least in the piercing means, the second event resulting in the continued displacement of the channel forming device.

11. The device of claim 10 wherein the movement means further comprises a control knob operatively attached to the piercing means, wherein the piercing means can rotate, rotation of the piercing means being independently controlled with respect to the displacement of the piercing means and channel forming device.

12. The device of claim 11 wherein the piercing means comprises a guiding member, whereby the guiding member guides the channel forming device to facilitate formation of branched revascularization channels in tissue.

13. A hand held auto-piercing mechanism comprising:

a handle assembly having a head portion whose distal end is configured to engage tissue;

a channel forming device extending through the handle assembly and head portion;

a piercing means surrounding the channel forming device for making an initial opening in tissue; and a movement means operatively attached to the piercing means and the channel forming device for independently controlling the movement of the piercing means and the channel forming device, the movement means comprising a first displacement mechanism which advances and retracts the piercing means, and a second displacement mechanism which advances and retracts the channel forming device;

wherein the piercing means is wholly responsive to the movement means for making an initial opening in tissue.

14. The device of claim 13 wherein the first displacement mechanism comprises a thumbwheel and the second displacement mechanism comprises a side knob, wherein movement of the thumbwheel results in displacement of the piercing means, movement of the side knob results in displacement of the channel forming device.

15. The device of claim 14 wherein the first displacement mechanism further comprises a motor, and a first and second switching means operatively attached to the thumbwheel and the motor, wherein operation of the thumbwheel defines at least three operational modes, during a first of the at least three operational modes the first switching means is activated whereby the motor operates and the piercing means advances, during a second of the at least three operational modes the first and second switching means are deactivated and the piercing means is stationary, and during a third of the at least three operational modes the second switching means is activated whereby the motor operates and the piercing means retracts.

16. The device of claim 14 wherein the first displacement mechanism further comprises a motor, and a switching means operatively attached to the thumbwheel and the motor, wherein operation of the thumbwheel defines at least two operational modes, during a first of the at least two operational modes the switching means is activated whereby the motor operates and the piercing means advances and retracts in a reciprocating fashion, during a second of the at least two operational modes the switching means is deactivated and the piercing means neither advances nor retracts.

17. The device of claim 16 wherein the second displacement mechanism further comprises a depth stop control whereby the depth of the channel forming device in tissue can be set to preselect values.

18. The device of claim 16 further comprising a control knob operatively attached to the piercing means and the channel forming device therein, wherein the piercing means can rotate, rotation of the piercing means being independently controlled with respect to the first and second displacement mechanisms.

19. The device of claim 13 wherein the handle assembly further comprises at least one lumen, the at least one lumen having an opening at the distal end of the head portion and another opening which communicates with a vacuum source, whereby operation of the vacuum source results in secure engagement of the head portion with the tissue, assisted removal of ablated tissue, and increased blood flow into a channel formed by the channel forming device.

20. A handheld myocardial revascularization device comprising:

a handle assembly with a head portion whose distal end is configured to engage the heart;

a channel forming device extending through the handle assembly and head portion;

a piercing means surrounding the channel forming device for making an initial opening in tissue, the piercing means moves relative to the head portion and is translatable through the head portion; and an advancing means for controllably advancing the piercing means, the advancing means comprising an actuator means for advancing the piercing means, the actuator means comprising a thumbwheel attached to the handle assembly, a belt drive that rides on a pair of gear members, and a rotatably mounted needle piercing element that translates within one of the gear members bore with internal threads, whereby the advancing means enables initial tissue piercing.

21. A handheld myocardial revascularization device comprising:

a handle assembly with a head portion whose distal end is configured to engage the heart;

a channel forming device extending through the handle assembly and head portion;

a piercing means surrounding the channel forming device for making an initial opening in tissue, the piercing means moves relative to the head portion and is translatable through the head portion, the piercing means and the channel forming device moving independently with respect to one another; and an advancing means for controllably advancing the piercing means, the advancing means comprising an actuator means for advancing the piercing means, the actuator means comprising a motor operatively attached to the piercing means, whereby the advancing means enables initial tissue piercing.

22. The device of claim 21 wherein the actuator means further comprises a shaft operatively attached to the motor, the distal end of the shaft having a gear which engages and rotatably drives a rotatably mounted needle element.

23. The device of claim 22 wherein the gear is a worm gear.

24. The device of claim 22 wherein the gear is a bevel gear.

25. The device of claim 21 wherein the actuator means further comprises a shaft having a bladed end portion operatively attached to a spring-biased reciprocating needle element, whereby shaft rotations cause displacements of the needle element.

26. The device of claim 21 wherein the actuator means further comprises a translating shaft operatively attached to the motor, the translating shaft having a surface which engages a leaf-spring biased reciprocation needle element, whereby translating movements of the shaft cause displacements of the needle element.

27. The device of claim 21 wherein the actuator means further comprises a pivotal shaft, the distal end of the pivotal shaft engages a reciprocating needle element, whereby pivoting of the shaft cause displacements of the needle element.

28. The device of claim 27 wherein the pivotal shaft comprises a rack and pinion mechanism operatively attached to the needle, whereby the needle can be rotated and branched myocardial revascularization channels can be created.

* * * * *